(12) United States Patent
Wynden et al.

(10) Patent No.: US 11,107,559 B1
(45) Date of Patent: Aug. 31, 2021

(54) SYSTEM AND METHOD FOR IDENTIFYING ONE OR MORE INVESTIGATIVE SITES OF A CLINICAL TRIAL AND CENTRALLY MANAGING DATA THEREFROM

(71) Applicant: goBALTO Inc., San Francisco, CA (US)

(72) Inventors: Robert Wynden, San Francisco, CA (US); Jae Chung, San Francisco, CA (US)

(73) Assignee: GOBALTO, INC., San Francisco, CA (US)

(*) Notice: Subject to any disclaimer, the term of this patent is extended or adjusted under 35 U.S.C. 154(b) by 354 days.

(21) Appl. No.: 16/013,794

(22) Filed: Jun. 20, 2018

Related U.S. Application Data

(63) Continuation of application No. 14/530,341, filed on Oct. 31, 2014, now abandoned, and a continuation-in-part of application No. 13/089,396, filed on Apr. 19, 2011, now abandoned.

(51) Int. Cl.
```
G16H 10/40      (2018.01)
G06Q 50/22      (2018.01)
G06Q 30/02      (2012.01)
G06Q 30/08      (2012.01)
G06F 16/9535    (2019.01)
```

(52) U.S. Cl.
CPC ......... *G16H 10/40* (2018.01); *G06F 16/9535* (2019.01); *G06Q 30/0279* (2013.01); *G06Q 30/08* (2013.01); *G06Q 50/22* (2013.01)

(58) Field of Classification Search
CPC .............. G16H 10/40; G06F 16/9535; G06Q 30/0279; G06Q 30/08; G06Q 50/22
USPC ......................................................... 705/2–3
See application file for complete search history.

(56) References Cited

U.S. PATENT DOCUMENTS

| | | | |
|---|---|---|---|
| 2004/0249664 A1* | 12/2004 | Broverman | G06Q 10/067 705/2 |
| 2005/0256380 A1* | 11/2005 | Nourie | G16H 10/60 600/300 |
| 2014/0316793 A1* | 10/2014 | Pruit | G06F 19/00 705/2 |
| 2018/0301205 A1* | 10/2018 | Mao | G16H 10/20 |
| 2020/0020423 A1* | 1/2020 | Wu | G16H 10/60 |

* cited by examiner

*Primary Examiner* — Michael Tomaszewski
(74) *Attorney, Agent, or Firm* — Kraguljac Law Group, LLC

(57) ABSTRACT

A method and system for identifying one or more investigative sites (sites) of a clinical trial are described. Data may be received for a proposed clinical trial and deriving at least one key word term based on the data. Next, a search may be conducted in a biomedical database to uncover one or more codes associated with key word term(s). Subsequently, a health ontology mapper (HOM) boolean logic statement (bool) may be generated based on the one or more codes obtained from the biomedical database. The HOM bool is then transmitted to sites and/or accountable care organizations (ACOs) so each may conduct local searches using the HOM bool within local and restricted proprietary patient databases. Filtered matching patient data may be sent back to a sponsor. Prospective sites may be solicited for request for proposals (RFPs) in which one or more sites bid for the clinical trial.

14 Claims, 19 Drawing Sheets

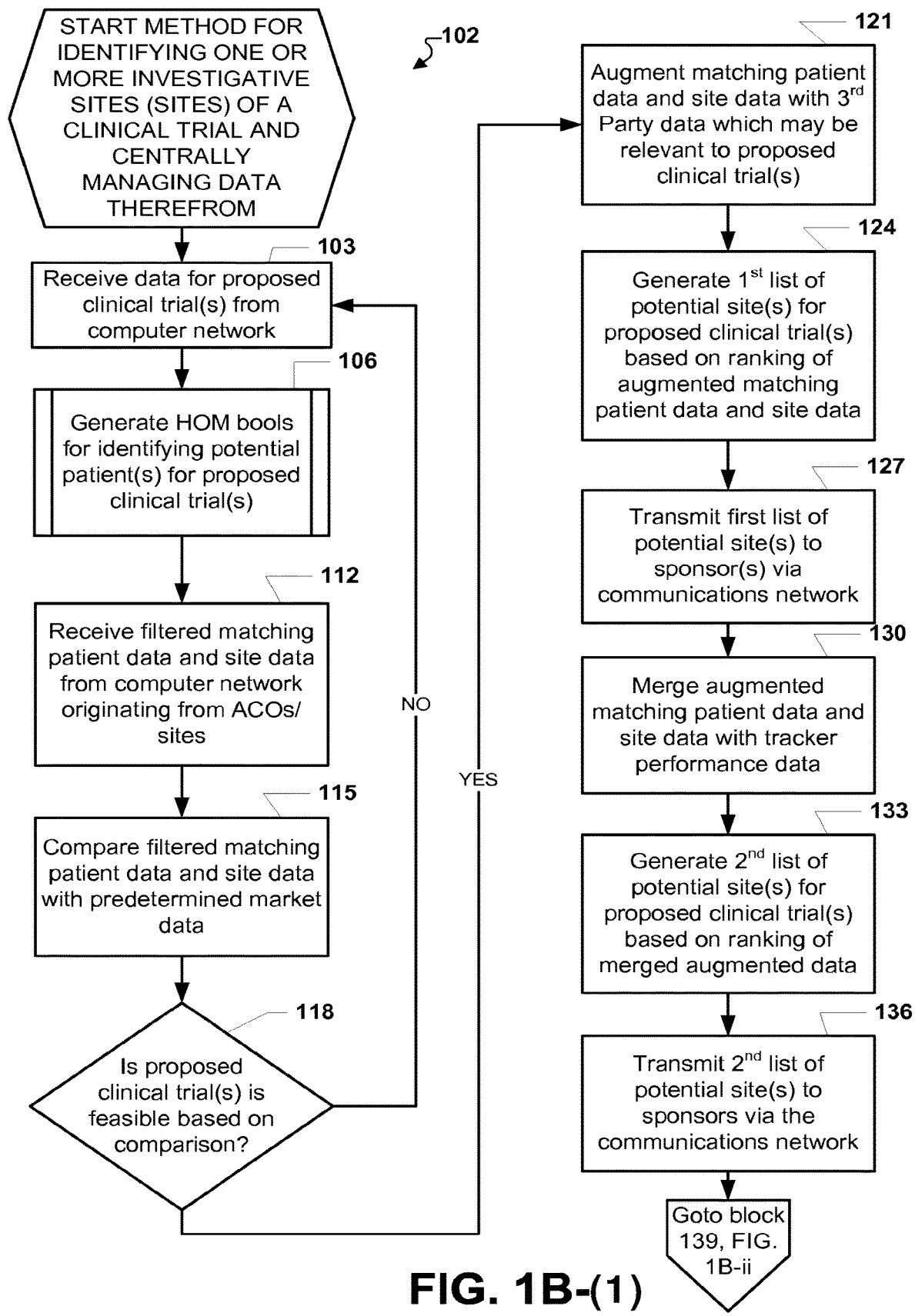
FIG. 1B-(1)

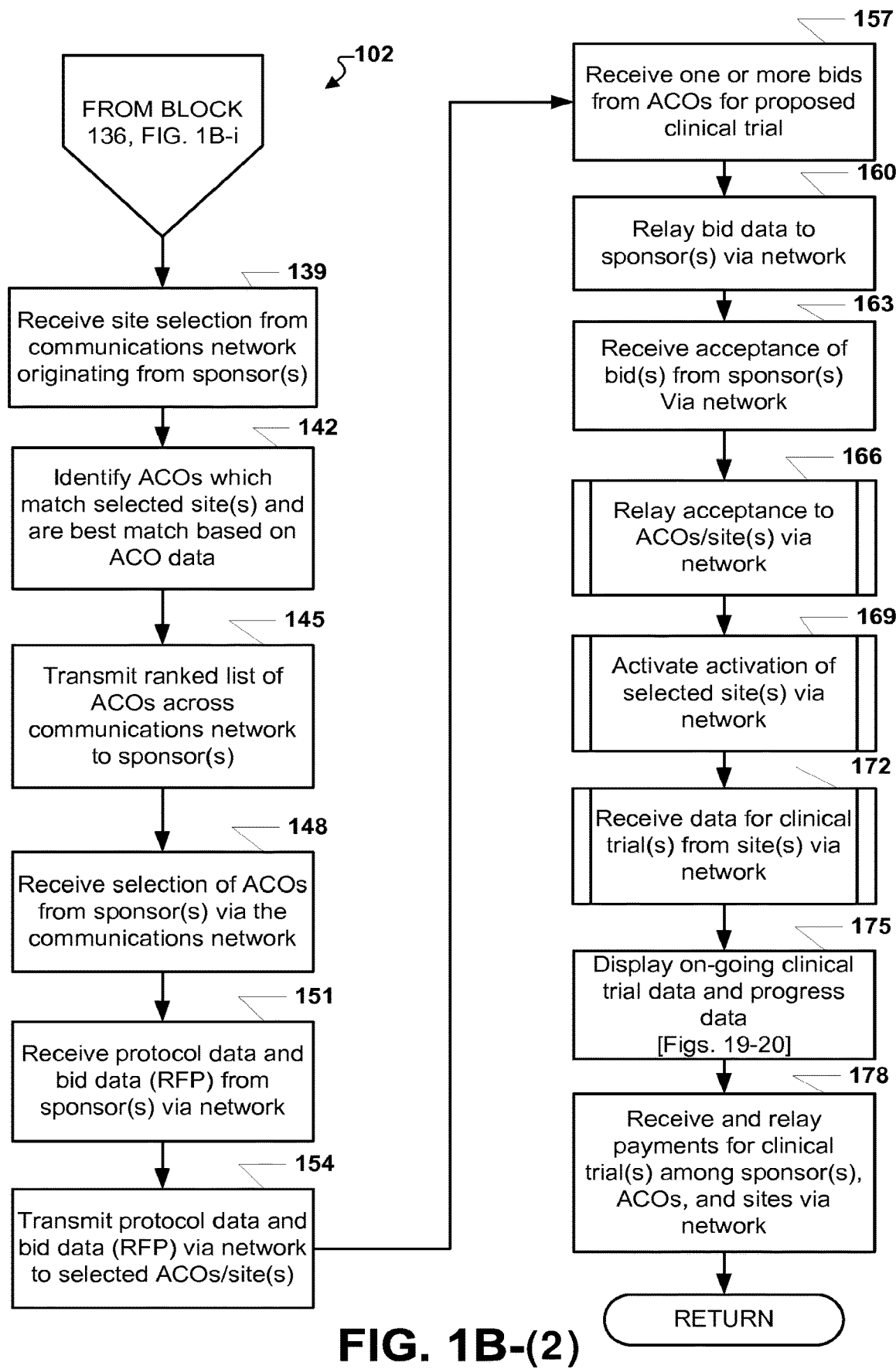
FIG. 1B-(2)

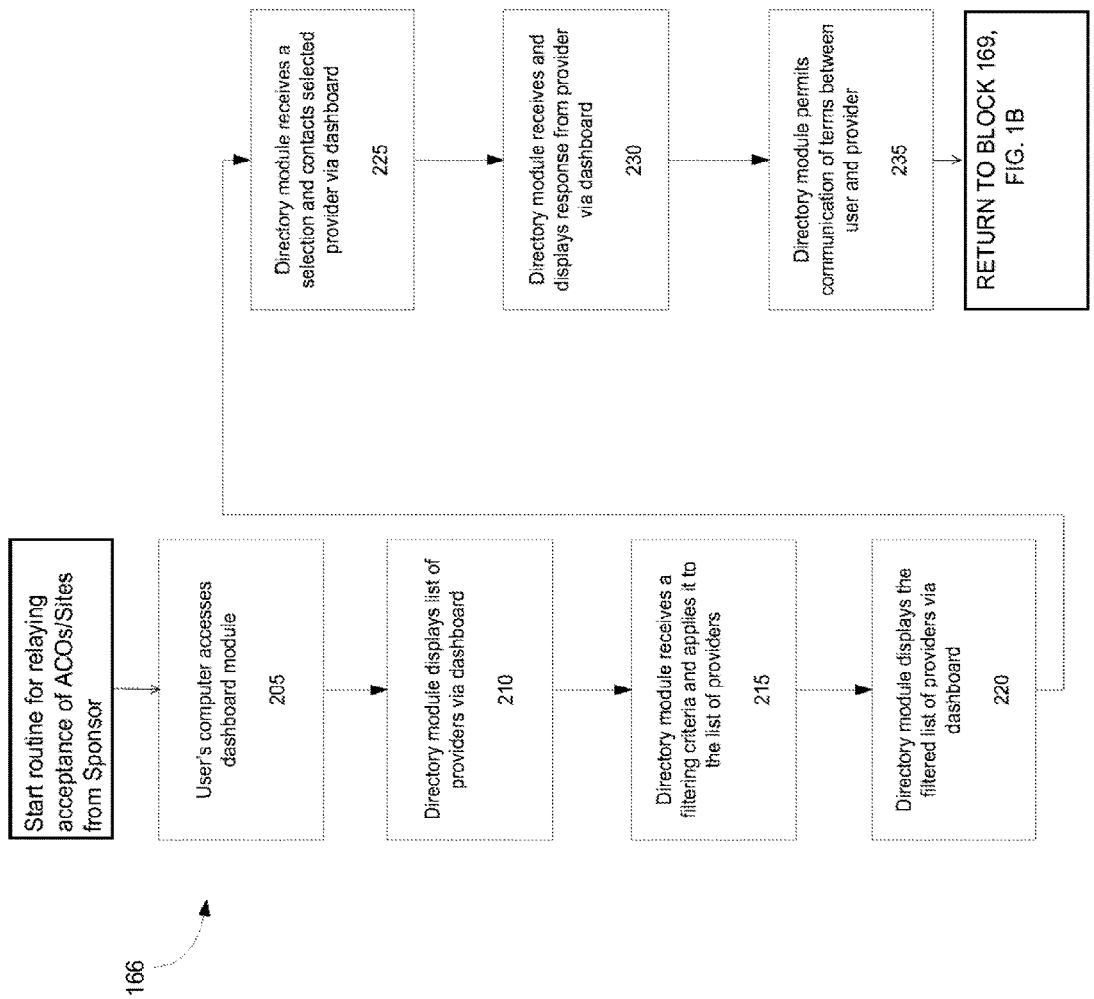

500

Title of Proposed Clinical Trial: New Surgical Procedure for Low Cervical Section

Abstract for Clinical Trial:

In this new surgical procedure, the patient is provided with Drug A, prior to surgery. Subsequently, the surgeon identifies the cervical section which will be the site of the surgery. Next....

- 
- 
-

Proposed Patients: Female, 22-32 years of Age, pregnant, no psychiatric illness, no prior cesarean sections performed on patient, ...

- 
- 
-

505

KEY TERMS (PROPOSED BY SPONSOR): low cervical section

FIG. 5

Patient 1     ↙ 800A
Name: Jane Doe
Address: 123 Chestnut Street
City: San Francisco
State: CA     Postal Code: 30065
Social Security Number: 215-92-2729     ╱ 605B
            ↙ 805B
Medical Diagnosis: SNOMED – C019562
Medical Notes: Hematoma post delivery in low cervical…

•
•
•

Patient 2     ↙ 800B
Name: Jane Deer
Address: 321 Hazelnut Street
City: San Francisco
State: CA     Postal Code: 30095
Social Security Number: 927-22-9512     ╱ 605A
            ↙ 805A
Medical Diagnosis: ICD – C10D00Z1
Medical Notes: Low PCB count post delivery in low cervical…

900A INVESTIGATIVE SITE DETAIL:
 SITE - NEW CASTLE: 45 Patients
 SITE Address: 44 Macon Street
905 SITE CITY: New Castle  STATE: CT  ZIP: 18106
 FACILITY AGE: 20 Years 1100 Total OBGYN specialists: 15
 Third Party Review Score of Facility: 8/10
 Patient Satisfaction Survey grade: 86%
 Law Suits within past 5 years: 2

FIG. 11

1200
900B TRACKER Ranked Listing of Sites based on 3rdP Augmented Data:
900A 1. Newtown: 65 patients
900C 2. New Castle: 45 patients
 3. San Diego Clinic: 54 patients

FIG. 12

900B TRACKER PERFORMANCE DATA / METRICS DETAIL:
 SITE: Newtown: 65 patients

1300 Number of Clinical Trials using Tracker System: 5
 Overall Percentage of timely data reporting for all clinical trials: 95%
 Overall Satisfaction rating with site from all sponsors: 85%
 Overall Number of Trials conducted: 156
 Number of Trials matching current HOM Bools: 2

SYSTEM AND METHOD FOR IDENTIFYING ONE OR MORE INVESTIGATIVE SITES OF A CLINICAL TRIAL AND CENTRALLY MANAGING DATA THEREFROM

RELATED APPLICATIONS STATEMENT

This application is a non-provisional patent application of and claims priority under 35 U.S.C. § 119(e) to U.S. Provisional Patent Application Ser. No. 61/899,086, filed on Nov. 1, 2013, entitled, "SYSTEM AND METHOD FOR IDENTIFYING ONE OR MORE INVESTIGATIVE SITES OF A CLINICAL TRIAL AND CENTRALLY MANAGING DATA THEREFROM." This application is also a continuation-in-part of and claims priority under 35 U.S.C. § 120 to U.S. patent application Ser. No. 13/089,396, filed on Apr. 19, 2011, entitled, "METHOD AND SYSTEM FOR WEB-BASED MANAGEMENT AND TRACKING OF CLINICAL TRIALS." The entire contents of these two patent applications are hereby incorporated by reference.

BACKGROUND

Accountable Care Organizations (ACOs) and other types of share-risk health organizations seek to lower the total cost of care for assigned populations of patients. Those patient populations are typically the highest cost drivers serviced by the member clinics and very significant overlap exists between those patient populations within ACO's and the patient markets targeted by biotech sponsor organizations for clinical trials.

ACO's may represent a Payer (insurance company) along with either a large clinical system or a collection of smaller clinics. As such ACO's represent aggregations of patients that could be targeted for study by biotech sponsors.

The revenue provided by clinical trials, as a means of paying for patient interventions, may result in an offset against the total cost of care for that population of patients. If an ACO can decrease the total cost of care by at least 2%, then shared savings are activated that can total as much as 60% of the total savings for the ACO. Those shared savings create a potentially large and untapped incentive for ACO's to attract large biotech clinical trials.

In view of this background, what is needed is a method and system which can facilitate the interaction between sponsors of clinical trials and investigative sites as well as ACOs in which sites and ACOs may bid for clinical trials in a cost-effective and efficient manner.

SUMMARY OF THE DISCLOSURE

A method and system for identifying one or more investigative sites of a clinical trial and centrally managing data received from the investigative sites are described. The system and method include receiving data for a proposed clinical trial from a communications network and deriving at least one key word term based on the data. Next, a search may be conducted in a biomedical database to uncover one or more codes associated with the at least one key word term. Subsequently, a health ontology mapper (HOM) boolean logic statement may be generated based on the one or more codes obtained from the biomedical database.

The HOM boolean logic statement is then transmitted over the communications network such that the investigative sites and/or accountable care organizations (ACOs) may conduct local searches using the HOM boolean logic statements within proprietary patient databases. After these local searches are conducted, filtered matching patient data may be received by a sponsor from the communications network. This filtered matching patient data usually does not have any restricted or proprietary information.

Next, a list of one or more proposed investigative sites may be generated based on the filtered matching patient data and site data collected by a tracker server. Prospective sites may then be solicited for submitting requests for proposals (RFPs) in which one or more sites may bid for the clinical trial. Specifically, protocol data and bid data may be transmitted over the communications network to the one or more selected investigative sites. Next, one or more bids on the proposed clinical trial may be received from the communications network that originate from one or more investigative sites and/or ACOs.

Acceptance of the one or more bids may be relayed over the communications network. One or more investigative sites may then be activated on the server corresponding to the accepted bids.

Data for the one more investigative sites monitored by the tracker server may be augmented with third-party data. Such third-party data may include, but is not limited to, medical professional specialties for a site, medical professional evaluations for staff of a site, reviews of a facility for a site, and a ranking of the investigative site and/or its medical professionals from patients. The method and system may rank the one or more proposed investigative sites based on the third-party data to assist in the selection process for feasible investigative sites to support a clinical study.

BRIEF DESCRIPTION OF THE DRAWINGS

In the Figures, like reference numerals refer to like parts throughout the various views unless otherwise indicated. For reference numerals with letter character designations such as "102A" or "102B", the letter character designations may differentiate two like parts or elements present in the same Figure. Letter character designations for reference numerals may be omitted when it is intended that a reference numeral encompass all parts having the same reference numeral in all Figures.

FIGS. 1B-(1) and 1B-(2) illustrate an automated method for identifying clinical trial sites for a clinical trial and centrally managing data received from the clinical trial sites using the system illustrated in FIG. 1A;

FIG. 2 illustrates a submethod or routine of FIG. 1B for relaying an acceptance from a sponsor of an offer by an accountable care organization (ACO) for a proposed clinical trial;

FIG. 5 illustrates exemplary data that may be provided by a sponsor for a proposed clinical trial;

FIG. 8 illustrates exemplary proprietary patient data that may be maintained by sites as well as ACOs in their respective proprietary databases which are not available to the public and are restricted;

FIG. 11 illustrates third party site data which may be added by the tracker server to existing site data and matching patient data;

FIG. 12 illustrates a first ranked list of potential sites generated by the tracker server for a proposed clinical trial based on the ranking of augmented matching patient data and site data;

FIG. 13 illustrates site performance data which may be tracked by the tracker server of FIG. 1A;

FIG. 19 illustrates a user interface that may be accessed over the computer network of FIG. 1A by one or more sponsors for managing clinical sites;

FIG. 20 illustrates a user interface that may be accessed over the computer network by a single or individual clinical site.

DETAILED DESCRIPTION

The word "exemplary" is used herein to mean "serving as an example, instance, or illustration." Any aspect described herein as "exemplary" is not necessarily to be construed as preferred or advantageous over other aspects.

In this description, the term "application" may also include files having executable content, such as: object code, scripts, byte code, markup language files, and patches. In addition, an "application" referred to herein, may also include files that are not executable in nature, such as documents that may need to be opened or other data files that need to be accessed.

The term "content" may also include files having executable content, such as: object code, scripts, byte code, markup language files, and patches. In addition, "content" referred to herein, may also include files that are not executable in nature, such as documents that may need to be opened or other data files that need to be accessed.

As used in this description, the terms "component," "database," "module," "system," and the like are intended to refer to a computer-related entity, either hardware, firmware, a combination of hardware and software, software, or software in execution. For example, a component may be, but is not limited to being, a process running on a processor, a processor, an object, an executable, a thread of execution, a program, and/or a computer. By way of illustration, both an application running on a computing device and the computing device may be a component.

One or more components may reside within a process and/or thread of execution, and a component may be localized on one computer and/or distributed between two or more computers. In addition, these components may execute from various computer readable media having various data structures stored thereon. The components may communicate by way of local and/or remote processes such as in accordance with a signal having one or more data packets (e.g., data from one component interacting with another component in a local system, distributed system, and/or across a network such as the Internet with other systems by way of the signal).

Sponsors. As used herein, the term "sponsors" refers to companies or organizations/entities that sponsor or fund clinical trials. Sponsors may also include contract research organizations (CROs).

Accountable Care Organizations (ACOs) and other types of share-risk health organizations are hereby collectively referred to as ACO's. ACOs seek to lower the total cost of care for assigned populations of patients. Those populations are typically the highest cost drivers serviced by member clinics and very significant overlap exists between those patient populations within ACO's and the patient markets targeted by sponsors for clinical trials.

ACO's may comprise a Payer (insurance company) along with either a large clinical system or a collection of smaller clinics. As such, ACO's represent aggregations of patients that could be targeted for study by sponsors.

Figure 1A:
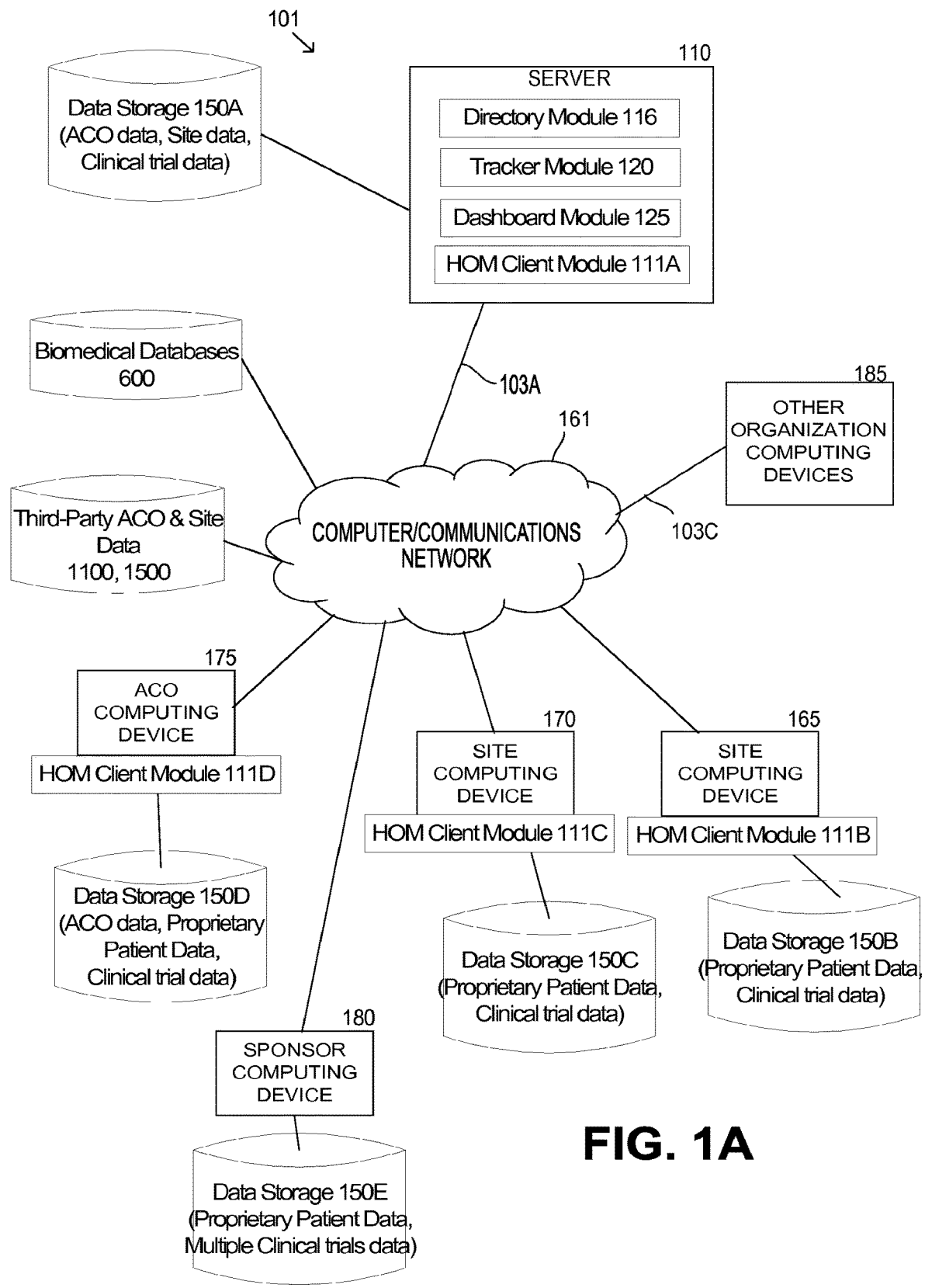
FIG. 1A illustrates a system for identifying investigative sites in a clinical trial and centrally managing data received from the investigative sites.

Referring to FIG. 1A, this figure illustrates a system 101 for identifying clinical trial sites 165, 170 for a clinical trial and centrally managing data received from the clinical trial sites 165, 170. The exemplary architecture of FIG. 1 may comprise a series of software modules installed and operating on a server computer 110.

The software modules installed on the server computer 110 can include a directory module 115, a tracker module 120, a dashboard module 125, and a health ontology mapper (HOM) client module 111A. In other embodiments, these modules can be combined or further divided into more detailed software modules.

The directory module 115 may permit sponsors 180 to locate and communicate with providers of services including ACOs 175 as well as investigative sites 165, 170 for performing clinical trials. For the remainder of this disclosure, sites 165, 170 as well as sponsors 180 and ACOs 175 will be referenced as performing certain tasks or method steps.

However, it is understood by one of ordinary skill in the art that each site 165 and 170 as well as sponsor 180 and ACO 175 may comprise a computing device, similar to tracker server 110, which may complete these tasks or steps.

In other words, while sites 165, 170; sponsors 180; and ACOs 175 may be described as completing certain steps or tasks described below, it is apparent to one of ordinary skill in the art that a machine, such as a computing device operated and programmed by personnel of these organizations, may complete some or all of these steps or tasks.

The tracker module 120 running on tracker server 110 may allow sponsors 180 to track the status of documents and action items associated with one or more studies (i.e. clinical trials) performed by one or more investigative sites 165, 170.

The dashboard module 125 may provide a user interface for a sponsor 180 to access and receive information from the directory module 115, the tracker module 120, or other software modules. The server computer 110 may comprise a conventional computing device that includes one or more processors, a memory, and various input and output devices as will be described in further detail below in connection with FIG. 21.

Figure 7:
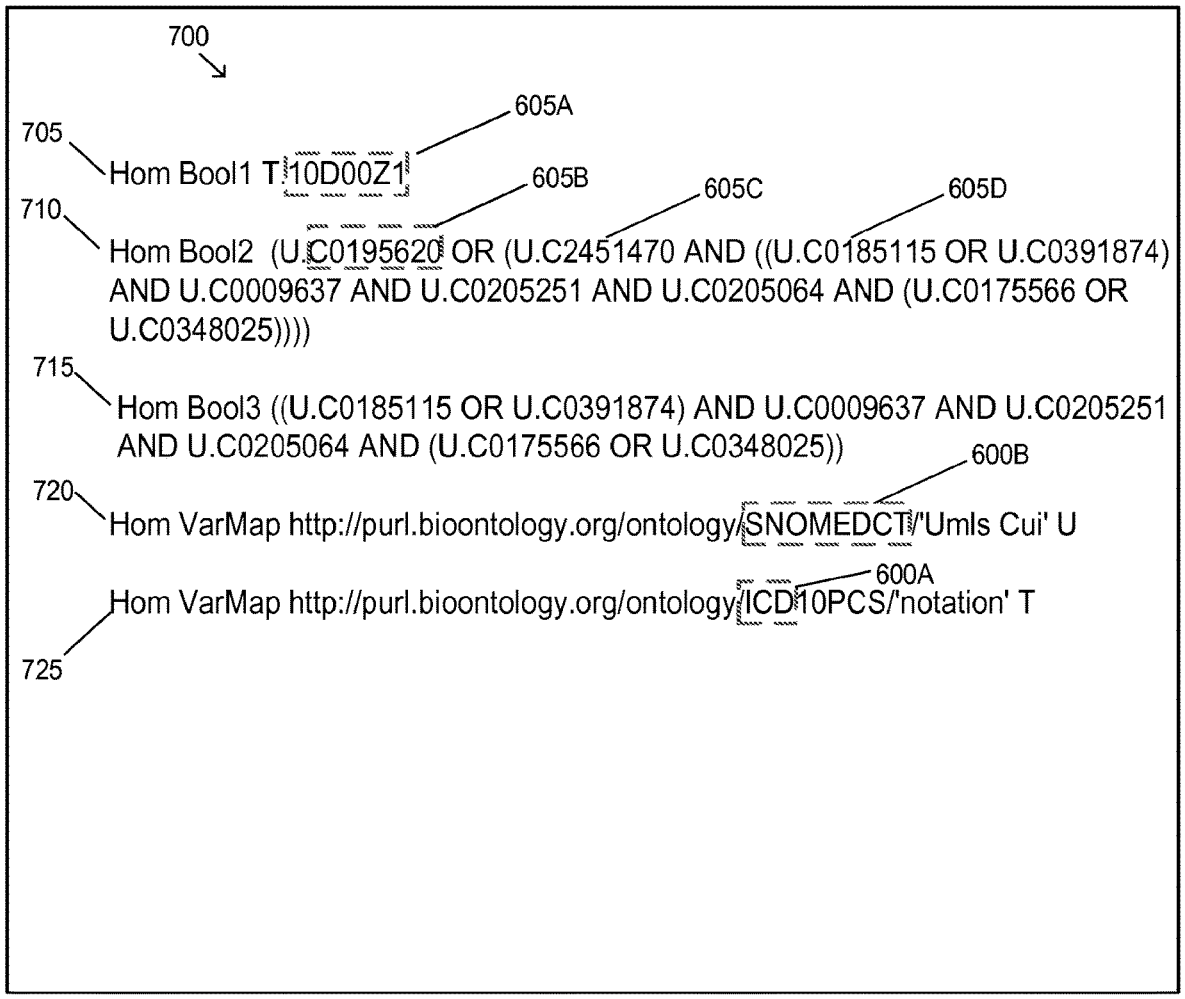
FIG. 7 illustrates an exemplary embodiment of HOM bools based on the data for the proposed clinical trial outlined in FIG. 5.

The HOM client module 111A may comprise off-the-shelf software for executing searches in medical data using one or more HOM boolean logic statements (bools) 700 (See FIG. 7). HOM bools 700 may be generated for identifying potential patient(s) for one or more proposed clinical trials. Further details about HOM bools 700 are described below in connection with FIG. 7.

In FIG. 1A, tracker server computer 110 is coupled to a first data storage device 150A. The first data storage device 150A may maintain data used by the directory module 115, the tracker module 120, the dashboard module 125, or the HOM client module 111A. The data stored in the storage device 150A may comprise data about sponsors 180, ACOs 175, and sites 165, 170. The data may further include profile data describing the sponsors 180, ACOs 175, and sites 165, 170, other organizations 185, and the services they offer. The data stored in the first storage device 150A may also comprise documents and tasks associated with clinical studies completed by sites 165, 170.

Server 110 also may also be coupled via a network connection to a communications network 161. Each of the elements of the system 101, including the server 110, are coupled to the computer communications network 161 via communication links 103.

The communication links 103 illustrated in FIG. 1A may comprise wired or wireless communication links. Wireless communication links include, but are not limited to, radio-frequency ("RF") links, such as, BLUETOOTH™ RF links, WIFI™ RF links, as well as infrared links, acoustic links, and other wireless mediums. The computer communications network 161 may comprise a wide area network ("WAN"), the plain-old-telephone-system ("POTS), a local area network ("LAN"), the Internet, or any combination of these and other networks.

The communications network 161 permits the sponsors 180, ACOs 175, sites 165, 170, and other organizations 185 to communicate with the tracker server 110 and the software modules installed thereon.

Other service organizations, represented by the other organization computing device 185, may communicate with the tracker server 110 as well as the other servers and may provide services in biomedical and pharmaceutical industries, such as manufacturing and consulting. Such other organizations may not participate in clinical trial startup projects, but may offer related services.

The computing devices 165, 170, 175, 180, and 185 for the various organizations may comprise similar hardware and software, like that of tracker server 110, as will be described in further detail below in connection with FIG. 21.

The sites (computing devices) 165, 170 each may be coupled to respective proprietary second and third data storage devices 150B, 150C. These second and third data storage devices 150B, 150C may contain privileged and legally protected, proprietary patient data 800 (See FIG. 8). The second and third data storage devices 150B, 150C may have restricted access such that only server 165 or server 170 may gain access to this proprietary patient data 800.

Each site 165, 170 may also have a respective local HOM client module 111B, 111C. Each HOM client module 111B, 111C may be capable of executing searches within the proprietary patient data 800 stored in second and third storage devices 150B, 150C using HOM bools 700, similar to the HOM client module 111A of tracker server 110.

The ACO (ACO computing device) 175 may also be coupled to a fourth storage device 150D. An ACO 175 may be responsible and may have control over the one or more sites 165, 170. So this means that the ACO 175 may have access to the proprietary patient data 800 stored on the second and third storage devices 150B, 150C. The ACO 175 may also have access to its own proprietary data stored on the fourth storage device 150D. The proprietary data stored on the fourth storage device 150D may comprise data unique to an ACO 180 and may include information about financials, patient data 800, clinical trial data, services, ratings and the like regarding sites 165, 170.

The ACO 175 may also have a respective local HOM client module 111D so that the HOM module 111D may be capable of executing searches within the proprietary patient data 800 stored in second and third storage devices 150B, 150C, as well as in the fourth storage device 150D using HOM bools 700.

The sponsor (sponsor computing device) 180 may be coupled to a fifth data storage device 150 for storing its own proprietary data. Such proprietary data may include, but is not limited to, details about respective clinical trials, clinical trial data, protocols for clinical trials, information on ACOs 175 and sites 165, 170, etc.

The system 101 may further include biomedical databases 600 and third-party ACO/site databases 1100, 1500 which are coupled to the communications network 161. The biomedical databases 600 may include, but are not limited to, the International Classification of Diseases (also known by the abbreviation ICD) as well as the Systematized Nomenclature Of Medicine (SNOMED) Clinical Terms (CT). Other biomedical databases 600 exist as of this writing as well as others which have not been created. This disclosure covers existing as well as future biomedical databases 600 not yet created. Further details of the biomedical databases 600 will be described below in connection with FIG. 6.

Third-party site data stored in database 1100 may include, but is not limited to, medical professional specialties, medical professional evaluations, faculty reviews, past or present litigation against sites and/or employees of a site 165, 170, consumer/patient reviews of sites 165, 170, etc.

Third party ACO data stored in database 1500 may include, but is not limited to, financial health or well-being of an ACO 175, ranking of an ACO 175 in an ACO community, and ranking of ACOs 175 by other sponsors who have conducted clinical trials with a particular ACO 175. Other site data 1100 and ACO data 1500 may exist as of this writing as well as others which have not been created. This disclosure covers existing as well as future site and ACO databases 1100, 1500 not yet created. Further details about site data 1100 and ACO data is described below in connection with FIGS. 11 and 15.

The architecture illustrated in FIG. 1 is merely illustrative and it will be obvious to those skilled in the art that the invention can be implemented in a variety of computing environments and/or contexts.

Brief Overview of System 101

A sponsor 180 which is looking for potential patients and ideal investigative site(s) 165, 170 for a new, proposed clinical trial may communicate information about the proposed clinical trial over the communications network 161 to the tracker server 110. This information may comprise an abstract describing high level aspects of the proposed clinical trial. Based on the received information about the proposed clinical trial, the tracker server 110 alone, and/or in combination with a human operator, may generate HOM bools 700 (See FIG. 7) by accessing the biomedical databases 600 as will be described in more detail below.

The tracker server 110 may then relay the HOM bools 700 over the communications network to one or more sites 165, 170 and/or ACOs 175. Each site 165, 170 and/or ACO 175 may execute a search within its respective proprietary patient data 800 stored on the second, third, and fourth data storage devices 150B-D using the HOM bools 700 with its respective HOM client module 111.

Each respective HOM client module 111 can identify respective matching patient data 800. Each site 165, 170 and ACO 175 may filter this matching patient data 800 so that only raw numbers (filtered patient data 900—See FIG. 9) not containing any proprietary or legally protected information is sent over the communications network 161 back to the tracker server 110. The tracker server 110 can then relay these raw numbers (filtered patient data 900) and any relevant site data to the sponsor 180 over the communications network 110.

Based on the raw numbers or filtered patient data 900, the sponsor 180 may select one or more sites 165, 170 which may be eligible/capable of conducting the clinical trial. The tracker server 110 may transmit protocol data and bid data (i.e. request for proposals [RFPs], etc.) over the communications network 161 to the one or more sites 165, 170. The one or more sites 165, 170, after receiving and evaluating the protocol data and bid data (RFP data), may submit bids to the tracker server 110 over the communications network 161.

The bids may contain monetary offers in order to secure the proposed clinical trial from the sponsor 180. For the sites 165, 170 in which the sponsor 180 accepts a respective bid, the tracker server 110 may monitor and track a clinical trial data received from the sites 165, 170 using the tracker module 120 and dashboard module 125.

Method 102 of FIG. 1B

FIG. 1B illustrates an automated method 102 for identifying clinical trial sites 165, 170 of a clinical trial and centrally managing data from the clinical trial sites 165, 170 using system 101 illustrated in FIG. 1A. The first step of method 102 begins with block 103. In block 103, data 500 (See FIG. 5) for one or more clinical trials is received by the tracker server 110 from a sponsor 180 via the computer network 161. The data 500 received may comprise information about a proposed clinical trial. Exemplary data 500 is described in further detail below in connection with FIG. 5. Generally, the data 500 for a proposed clinical trial usually comprises sufficient information for generating one or more key terms 505 that may be useful for searching biomedical databases.

Next, in routine or sub-method block 106, Health Ontology Mapper (HOM) boolean logic statements (bools) 700 are generated for identifying potential patient(s) for one or more proposed clinical trials. HOM bools 700 may comprise pseudo computer code-like statements that may be executed by a HOM client 111 for searching a biomedical database 600. The HOM bools 700 usually comprise numeric or alphanumeric codes 605 which may be derived from the key terms 505 described above. Further details about HOM bools 700 and biomedical database codes 605 are described below in FIGS. 6A-6B and 7.

The HOM bools 700 may be automatically generated by the tracker server 110 and/or generated manually in this routine block 106. Further details of routine block 106 are described below in connection with FIG. 5.

Subsequently, after routine block 106, in routine block 109, the HOM bools 700 are transmitted over the computer network 161 from the tracker server 110 to one or more accountable care organizations (ACOs) 175. At the ACOs 175, searches for patient data matching the HOM bools 700 may be conducted by HOM clients 111. Each ACO 175 may have its own HOM client 111 residing on its computing device which may allow an ACO 175 to conduct code searches in its own proprietary data storage 150D. The proprietary data storage 150D may comprise confidential patient data which may be protected by laws, such as Health Insurance Portability and Accountability Act (HIPAA) found in the United States or The European Union's (EU) Data Protection Directive.

Further details of routine block 109 are described below in connection with FIG. 1D. Routine block 109 constitutes one of the many important aspects of the inventive system 101. Specifically, the HOM bools 700 which are received by each ACO 175 allows each ACO to conduct its own research of its own proprietary patient data 800A (See FIG. 8), so that restricted patient data, such as information maintained in the United States and restricted by HIPAA, is never transmitted over the computer network 161 back to either the tracker server 111 or sponsor 180.

The filtered patient data 900 which is transmitted over the computer network 161 as a result of routine block 109 may comprise data on amounts or numbers of matches which were found. Personal and/or identifying information that may be found in patient data is never transmitted over the computer network 161. Such personal and/or identifying information, which may be restricted, is filtered during routine block 109.

After routine block 109, in block 112, the tracker server 111 may receive the filtered matching patient data 900 as well as site data 905 (FIG. 9) from the computer network 161 originating from an ACO 175. Next, in block 115, the filtered matching patient data 900 and site data 905 may be compared with predetermined marketing data 1000 such as illustrated in FIG. 10.

Figure 10:
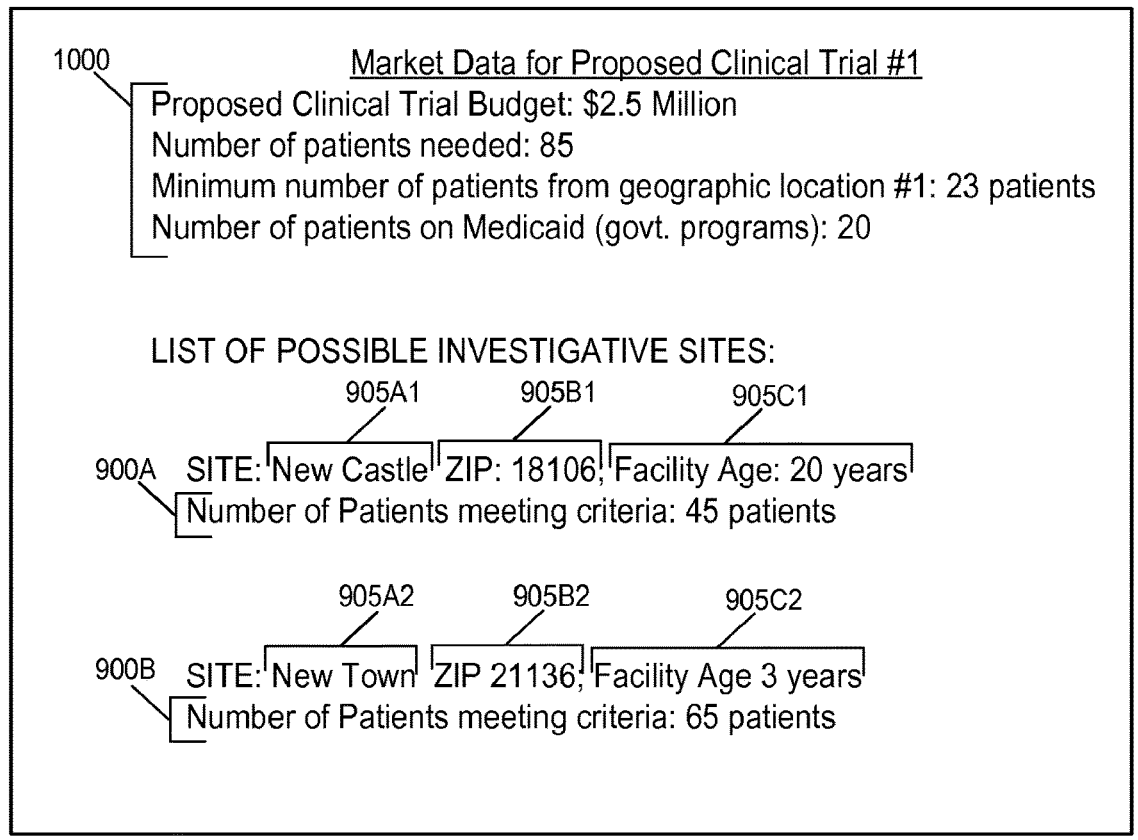
FIG. 10 illustrates predetermined marketing data which may be prepared by a sponsor in advance of conducting a patient search for a proposed clinical trial.

Referring briefly to FIG. 10, predetermined marketing data 1000 may be prepared by a sponsor 180 in advance of conducting a patient search. Predetermined marketing data 1000 may include, but is not limited to, monetary budget, number of patients needed, and other data relevant to the specifics of a particular clinical trial. For example, other data in the predetermined marketing data 1000 illustrated in FIG. 10 may include minimum number of patients from a particular geographic area (such as a postal zip code) and minimum number of patients who subscribe to a government program (such as Medicaid in the United States). Other data may be included within the predetermined market data 1000 and is within the scope of this disclosure.

The market data 1000 may be keyed-in and stored and accessed by the tracker server 110. The comparison in block 115 between the market data 1000 and the filtered matching patient data 900 and site data 905 may be performed by the server 110. Alternatively, or in addition to the comparison made by the tracker server 110, operator (human) input may be received by the tracker server 110 in order to help with the comparison of data in this block 115.

In decision block 118, it is determined if the proposed clinical trial is feasible based on the comparison of marketing data in block 115. Usually, financial data may be a significant factor/variable that may influence a decision on whether a clinical trial should move forward.

If the inquiry to decision block 118 is negative, then the "NO" branch is followed back to block 103 in which a next proposed clinical trial may be evaluated. If the inquiry to decision block 118 is positive, then the "YES" branch is followed to block 121 in which matching patient data 900 and site data 905 may be augmented by the tracker server 110.

Specifically, in block 121, matching patient data 900 and site data 905 may be augmented by the tracker server 110 with third party data 1100 about sites 170 such as illustrated in FIG. 11. Third party site data 1100 may include, but is not limited to, medical professional specialties, medical professional evaluations, faculty reviews, past or present litigation against sites and/or employees of a site, consumer/patient reviews, etc. The tracker server 110 may add data fields to the site data 905 which may comprise this third party site data 1100.

Next in block 124, the tracker server 110 may generate a first list 1200 (See FIG. 12) of potential sites 170 for proposed clinical trial(s) based on a ranking of the augmented matching patient data and site data. The tracker server 110 may be programmed to assign different weights to each third party site data 1100. For example, a sponsor 180 may assign values for weighting each data field from third party data 1100 differently. For example, one sponsor 180 may give a higher weighting for facility age compared to past litigation history. Another sponsor 180 may have the reverse: giving a higher weighting to past litigation compared to facility age.

Next in block 127, the tracker server 110 may transmit the first list 1200 of potential sites 165, 174 the proposed clinical trial over the computer network 161 to the sponsor 180. Subsequently, in block 130, the tracker server 110 may merge the augmented matching patient data and site data with performance data 1300 (See FIG. 13) that is specifically monitored and maintained by the tracker server 110. Exemplary performance data 1300, may include, but is not limited to, number of clinical trials that a particular site 165, 170 has worked with the tracker server 110; overall percentage of timely data reporting for all clinical trials used with the tracker server 110; and overall satisfaction rating with the clinical site for all trials, etc.

Next, in block 133, the tracker server 110 may generate a second list 1400 of potential sites 165, 170 for the proposed clinical trial based on a ranking of the merged augmented data. The tracker server 110 may be programmed by each sponsor 180 to assign different weights to the performance data 1300. For example, a sponsor 180 may assign values for weighting each data field from performance data 1300 differently. For example, one sponsor 180 may give a higher weighting for reporting timeliness over the satisfaction rating of a particular site 165, 170. Another sponsor 180 may have the reverse: giving a higher weighting to the satisfaction rating of a site 165, 170 compared to its reporting timeliness during a clinical trial.

In block 136, the tracker server 110 may transmit the second list 1400 of potential sites 165, 174 proposed clinical trial based on a ranking of the merged augmented data over the computer network 161 to a particular sponsor 180. Next, in block 139, the tracker server 110 may receive selection of sites 165, 170 from the computer network 161 which originates from one or more sponsors 180 for the proposed clinical trial.

In response to receiving the selection of sites 165,170 from one or more sponsors 180 via the computer network 161, the tracker server 110 may then identify one or more ACOs 175 which match the selected sites 165, 170 and/or a best match based on ACO data 1500 (See FIG. 15) maintained by the tracker server 110. The tracker server 110 may keep an extensive database on ACO's 175 which manage and maintain particular sites 165, 170. Exemplary ACO data 1500 may include, but is not limited to, financial health or well-being of an ACO, ranking of an ACO in an ACO community, and ranking of ACO's by other sponsors who have conducted clinical trials with a particular ACO. Also in this block 137, the tracker server 110 may rank or identify best matches of ACOs 175 based on the ACO data 1500.

Next, in block 145, the tracker server 110 may transmit a ranked list of one or more matching identities of ACO's responsible for particular sites 165, 170 over the computer network 161 to the sponsors 180. Subsequently, in block 148, the tracker server may receive a selection of ACO's 175 from one or more sponsors 175 via a computer network 161.

In parallel, subsequent to, or prior to block 148, in block 151 the tracker server 110 may receive protocol data 1700 (See FIG. 17) from one more sponsors 175 via a computer network 161. The protocol data 1700 may comprise specific protocols or procedures that are needed by a clinical site 165, 170 to conduct a particular clinical trial. In block 151, the tracker server 110 may also receive bid data. The bid data may comprise an outline of information that highlights expectations that a sponsor 180 may have of any ACO 175 who desires to bid for a particular clinical trial.

Next, in block 154, the tracker server 110 may transmit protocol data 1700 as well as bid data via the computer network 161 to the ACO's 175 which were selected by a sponsor 180 as being eligible for a potential clinical trial. The bid data originating from the sponsor 180 may comprise incidental costs such as, but not limited to, medical supplies, medical services, accounting services, etc.

Subsequently, in block 157, the tracker server 110 may receive bid/offer data 1800 (See FIG. 18) from ACO's 175 via the computer network 161 for a proposed clinical trial. In block 160, the tracker server 110 may relay the bid/offer data 1800 to the sponsors 175 via the computer network 161. The bid/offer data 1800 from ACO's 175 may be in the form of monetary bids, however, other data may be submitted/offered such as medical services and medical supplies which may be provided by a particular ACO 175 and/or site 165, 170.

Subsequently, in block 163, the tracker server 110 may receive acceptance of one or more of the bid/offer data 1800 from one or more sponsors 175 via a computer network 161. Next, in routine or submethod 166, the tracker server 110 may relay the acceptance of the one or more bids 1800 to particular ACO's 175 via a computer network 161. Further details of routine 166 will be described below in connection with FIG. 2.

Subsequently, in routine 169, the tracker server 110 may initiate activation of selected sites 165, 170 for a proposed clinical trial. Further details of routine 169 will be described below in connection with FIG. 3.

After routine 169, in routine or submethod 172, the tracker server 110 may received test data for clinical trials from sites 165, 170 be the computer network 161. Further details of routine 172 will be described below in connection with FIG. 4.

After routine 172, in block 175, the tracker server 110 may display ongoing trial data via a user interface 1900 (See FIG. 19) and progress data 1910 for clinical sites 165, 170 and sponsors 180. Further details for the trial data tracked with a user interface 1900 and progress data 1910 will be described below in connection with FIGS. 19-20.

Next, in block 178, the tracker server 110 may received in relay payments for clinical trials from sponsors 182 ACO's 175 and/or sites 165, 170 via a computer network 161. After block 178, the method 102 then returns.

Figure 1C:
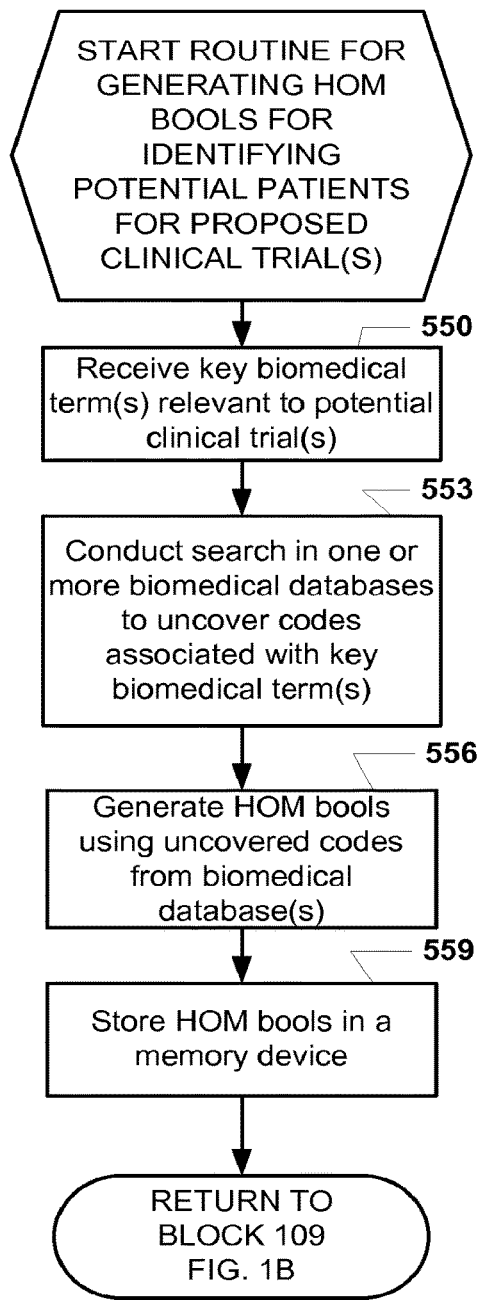
FIG. 1C illustrates a submethod or routine for generating Health Ontology Mapper (HOM) boolean logic statements (bools)

Referring now to FIG. 1C, this figure illustrates the submethod or routine 106 of method 102. Routine 106 is for generating HOM bools 700 which are illustrated in FIG. 7 and are described below.

Block 550 is the first step of submethod or routine 106. In block 550, the server 110 may receive one or more key biomedical terms 505 relevant to a potential clinical trial. In this block 550, the server 110 may search relevant fields of data for a proposed clinical trial. As noted previously, a sponsor 180 may supply key terms 505 as part of background information contained within the data for a proposed clinical trial.

Alternatively, or in addition to receiving key terms 505 from a sponsor 180, the server 110 may have searching software which may scan data on a proposed clinical trial and identify key terms 505 automatically. Further, a human operator who is an expert in an area relevant to a proposed clinical trial may also review the data and identify one or more key terms 505.

Subsequently, in block 553, the server 110 and/or a human operator may conduct a search in one or more biomedical databases to uncover codes 605 (See FIGS. 6A-6B). The codes 605 may be alpha and/or alphanumeric in nature and may be derived from the key terms 505 described above. Further details about the code 605 will be described below in connection with FIGS. 6A-6B.

Next, in block 556, the server 110 and/or a human operator may generate one or more HOM bools 700 (SEE FIG. 7) using the uncovered codes from block 553. Further details about HOM bools 700 will be described below in connection with FIG. 7.

And in block 559, the server 110 may store the HOM bools 700 in a memory device such as the data storage 150A as illustrated in FIG. 1A. The subroutine 106 then returns to routine block 109 of FIG. 1B.

Figure 1D:
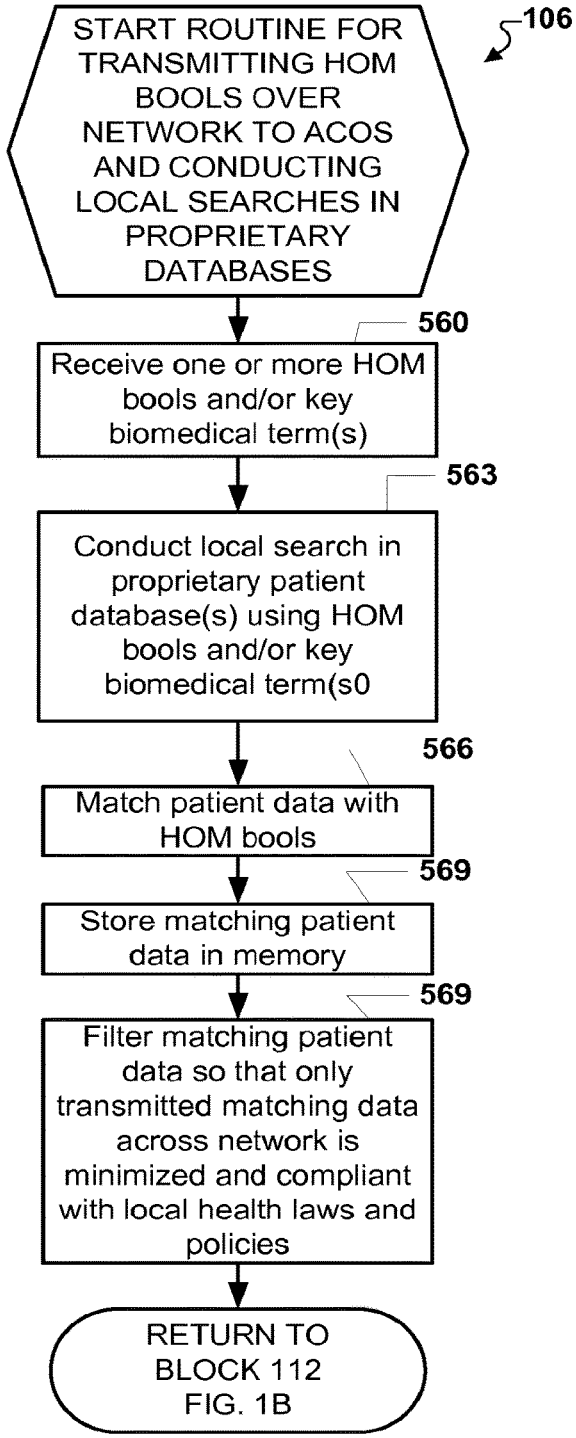
FIG. 1D illustrates a submethod or routine of method for transmitting HOM bools and conducting searches using the HOM bools.

Referring now to FIG. 1D, this figure illustrates a submethod or routine 109 of method 102. The routine 109 is for transmitting HOM bools 700 and conducting searches using the HOM bools 700.

Block 560 is the first block of routine 109. In block 560, one or more sites 165, 170 may receive the one or more HOM bools 700 from the computer network 161 originating from the tracker server 110. Next, in block 563, the one or more sites 165, 170 may conduct local searches within their proprietary databases 150E, F. These local searches may be executed by local HOM clients 111 running on local servers relative to the sites 165, 170.

As noted above, the local searches conducted within the proprietary databases 150E, F using the HOM bools 700 offers one of the several advantages to the inventive system 101. With each site 165, 170 conducting its own searches for potential matching patient data, there is little or no risk that protected or privileged information will be released outside the sites 165, 170.

Next, in block 566, the local computing device or local server of the site 165, 170 may match its patient data contained within its databases 150 E, F with the HOM bools 700 (See FIG. 8). Subsequently, in block 569, the site 165, 170 may store matching patient data 800 in a memory device. In block 572, each site 165, 170 may filter the matching patient data 800 to create filtered matching patient data 900 (See FIG. 9) so that the filtered matching patient data 900 is minimized and compliant with local health laws and local policies (i.e. HIPPA, etc.). According to one exemplary embodiment, the filtered matching patient data 900 may comprise a number that identifies a number of patients for a particular site 165, 170 that may match the one or more HOM bools 700 (See FIG. 9). The routine 109 then returns to block 112 of method 102 as illustrated in FIG. 1B.

FIG. 2 illustrates a submethod or routine 166 of FIG. 1D for relaying an acceptance from a sponsor 180 of an offer sent by an ACO 175 for a proposed clinical trial. Beginning with block 205, a member of the sponsor's team accesses the dashboard module 125 using sponsor computing device 180. The dashboard module 125 may provide an interface for the user to access the computer-implemented tools of the present invention.

In block 210, the directory module 115 may provide a list of potential providers of services for a new clinical trial study the sponsor 180 is initiating. The service providers can extend beyond those directly involved in the clinical trial study, such as manufacturers and consultants who can provide other related services. The directory module 115 can be used to assist various parties in the biomedical and pharmaceutical industry in making contacts and finding needed service providers 185. The dashboard module 125 may display the list of providers on the sponsor computing device 180.

In block 215, the directory module 115 may receive filtering criteria selected by an operator and apply the filter to the list in order to narrow the potential service providers. The filtered list of service providers may be displayed on the sponsor computing device 175 in block 220.

Once an operator of the sponsor computing device 180 has selected a service provider, such as a site 165, 170, the operator may enter the selection via the dashboard module 125 and the directory module 115 may contact the selected provider in block 225. For example, a site computing device 165, 170 may having access to dashboard module 125. In alternate embodiments, the sponsor 180 may contact the service provider, such as a site 165, 170, directly or using means other than the dashboard module 125 and the directory module 115.

In block 230, the directory module 115 may receive and display via the dashboard module 125 the response from the selected provider, such as a site 165, 170. For example, the response may include information about the provider's qualifications in addition to the information already stored in the provider's profile and accessible through the directory module 115.

The response may also include information about the provider's ability to provide services for the particular proposed clinical trial study. In block 235, the directory module 115 permits communication via the dashboard module 125 between the sponsor computing device 180 and a site's computing device 165, 170. For example, terms of services provided by the clinical sites may be negotiated and communicated using the dashboard module 125.

Figure 3:
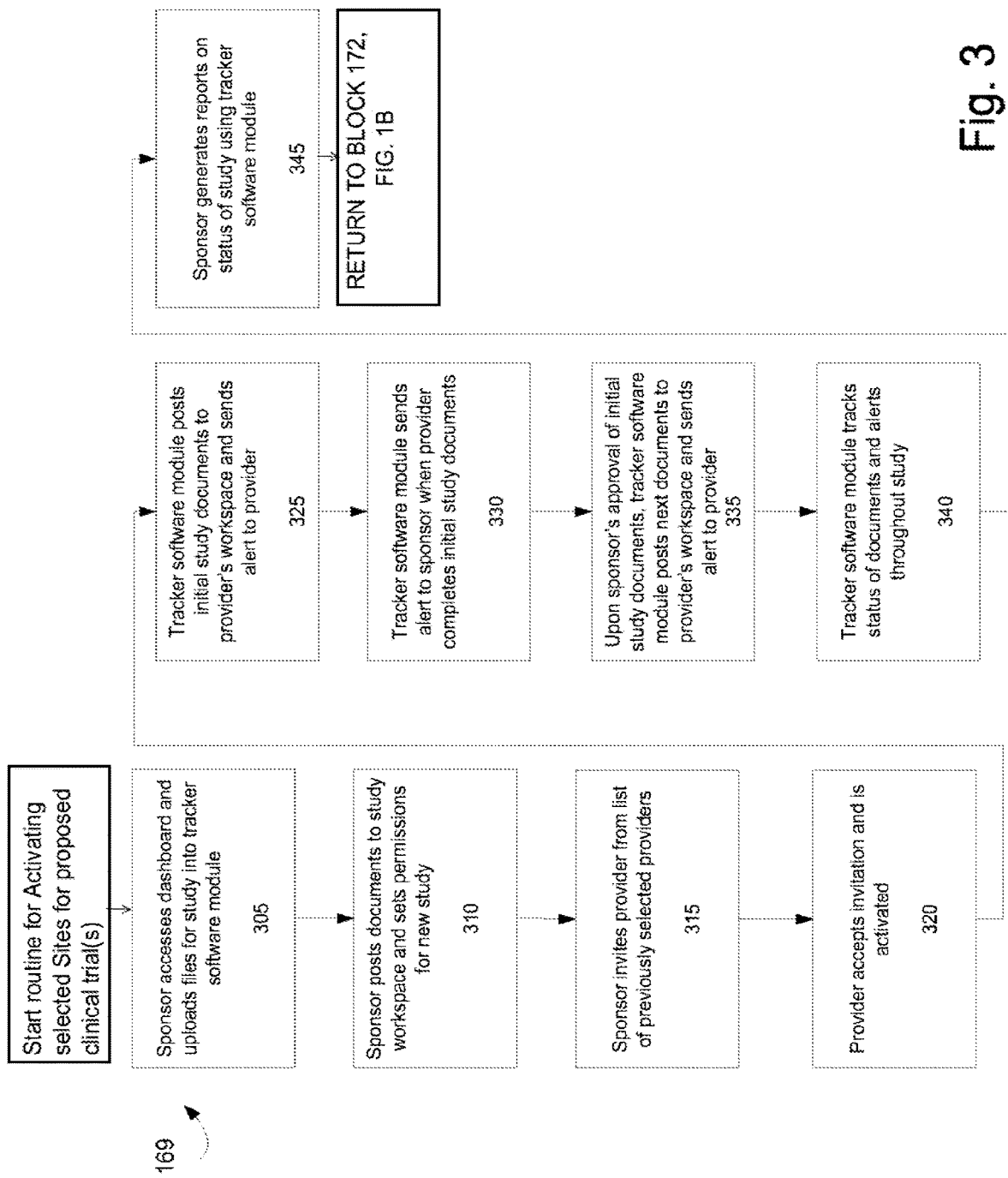
FIG. 3 illustrates a submethod or routine of FIG. 1B for activating one or more selected sites based on the offer accepted by the sponsor.

FIG. 3 illustrates a submethod or routine 169 of FIG. 1D for activating one or more selected sites 165, 170 based on the offer accepted by the sponsor 180. Block 305 is the first of routine 169. Block 305 begins with the sponsor computing device 180 gaining access to the dashboard module 125 and uploading files for the clinical study to the tracker software module 120 of server 110.

As described previously, the beginning of a clinical study typically will typically include the sponsor 180 adding metadata about the study to the site. The sponsor 180 can post one or more of the uploaded files, which typically are documents, to the sponsor's workspace on server 110 and can set permissions for accessing each of the documents in block 310.

In block 315 of exemplary routine 169, the sponsor 180 can invite a provider, such as an ACO 175 or site 165, 170 to begin providing services for the clinical trial study. In block 320, the ACO 175 or site 165, 170 may receive the invitation from the sponsor 180 via the computer network 161.

Figure 19:
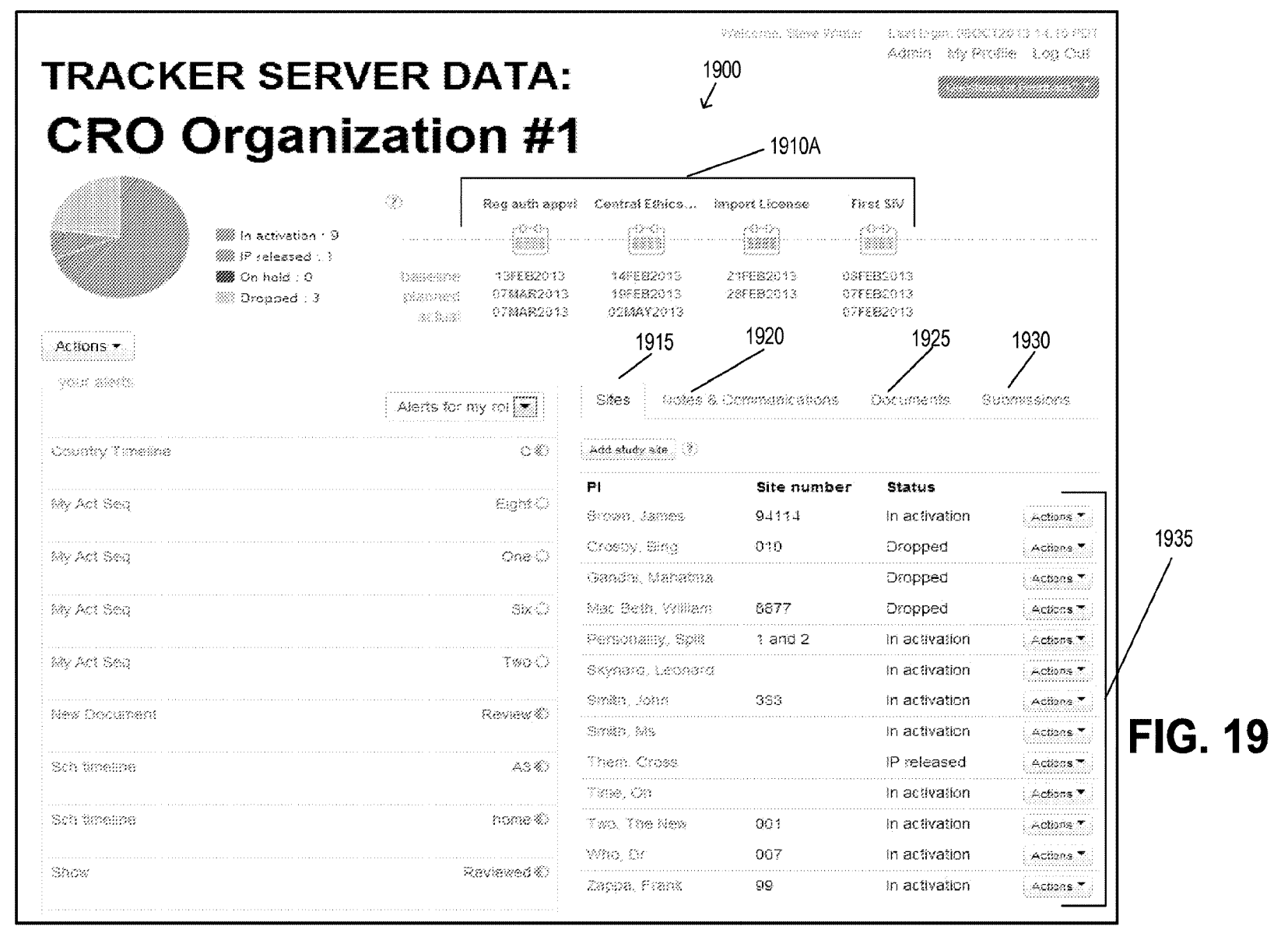
Figure 20:
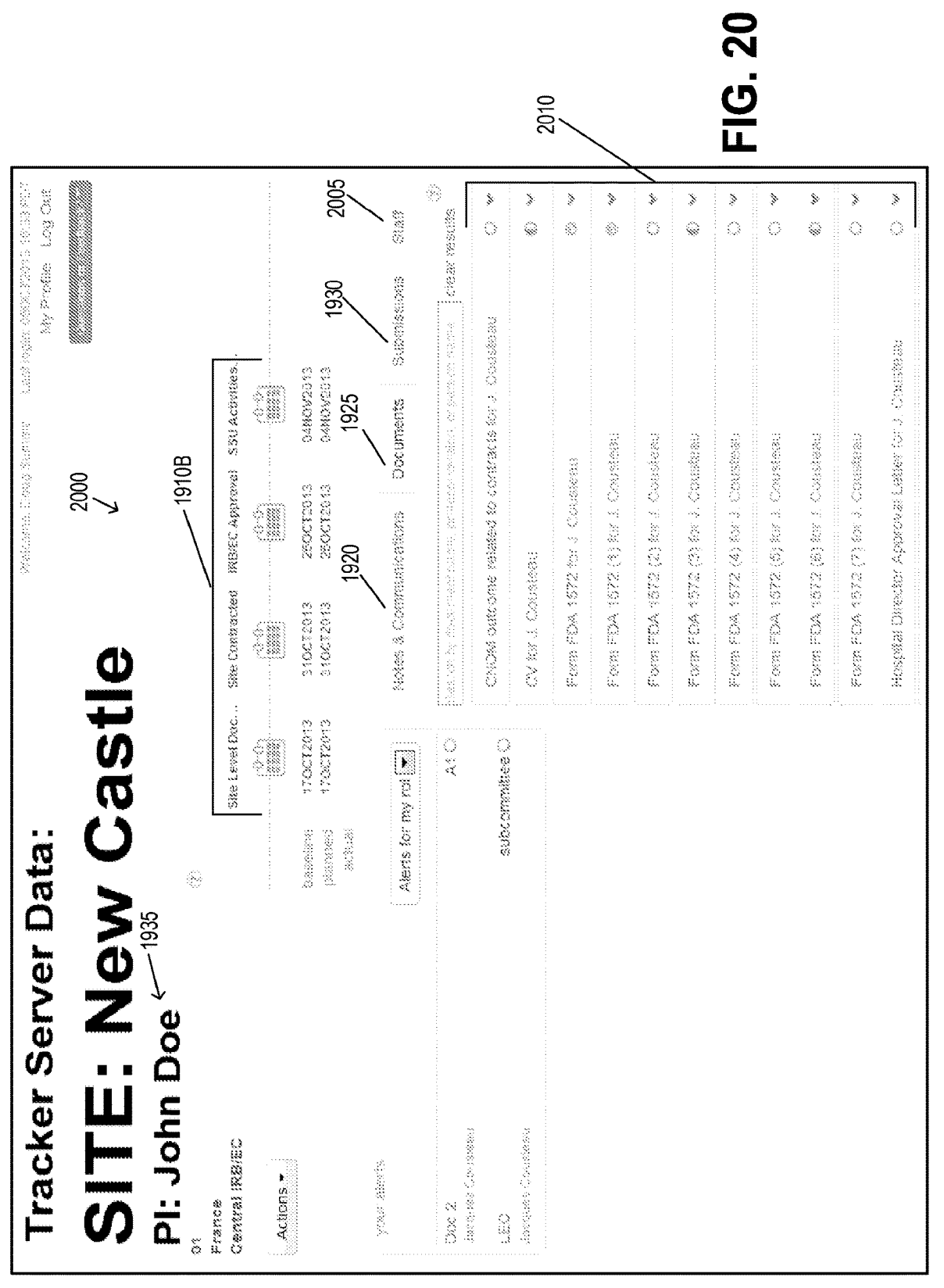

Once the provider has accepted the invitation, the provider (i.e. ACO 175 or site 165, 170) is activated within the tracker module 120. From this stage, the tracker software module 120 can assist with managing the workflow relating to the clinical trial study, such as illustrated in FIGS. 19-20 described below.

The tracker software module 120 running on the tracker server 110 may offer a variety of default and customizable workflows to assist sponsors 180, ACOs 175, and sites 165, 170 with managing the documents and tasks associated with a clinical study. For example, a default workflow can guide the sponsor 180 and investigative site 165, 170 with respect to the documents and tasks typically required with a particular type of study. Alternatively, the sponsor 180 or investigative site 165, 170 may choose to customize the workflow for a particular study.

Referring again to FIG. 3, in block 325, the tracker module 120 can post initial study documents to the provider's workspace maintained at the server 110 and send an alert to the provider, such as a site 165, 170. The alert can identify the posted documents and any tasks associated with the documents. The alert can be transmitted via the dashboard module 125 to the ACO 180 and/or sites 165, 170. When a provider completes the task or tasks associated with the initial clinical study documents, the tracker module 120 sends an alert to the sponsor 180 in block 330.

For example, the tracker module 120 can send, via the dashboard module 125 over the communications network 161, an alert to the sponsor 180. In block 335, upon a sponsor's review and approval of the initial study documents completed by the provider, the tracker module 120 can post the next set of study documents to the provider's workspace maintained at server 110 and send an alert to the provider (i.e. ACO 180 and/or sites 165, 170) over the communications network 161 regarding the newly posted documents and the associated open tasks.

The foregoing subprocess of routine 169 can continue through multiple stages or blocks of the clinical trial study as new documents and tasks arise. In block 340, the tracker module 120 can be used to monitor the status of documents, including changes to documents and newly posted documents, and to send alerts concerning tasks associated with the documents or the study.

Additionally, as indicated in block 345, the tracker module 120 can provide reports to the sponsor 180 concerning the status of documents and tasks associated with the clinical study, such as illustrated in FIGS. 19-20 described below. The reporting tools are not limited to a particular study, but can pull information, for instance, from multiple studies in a workspace.

For example, the reporting tool can be used to track the performance of a particular investigative site 165, 170 performing services for multiple clinical studies. As an additional example, for certain users with the appropriate access and permissions, reports can be generated from multiple workspaces.

Figure 4:
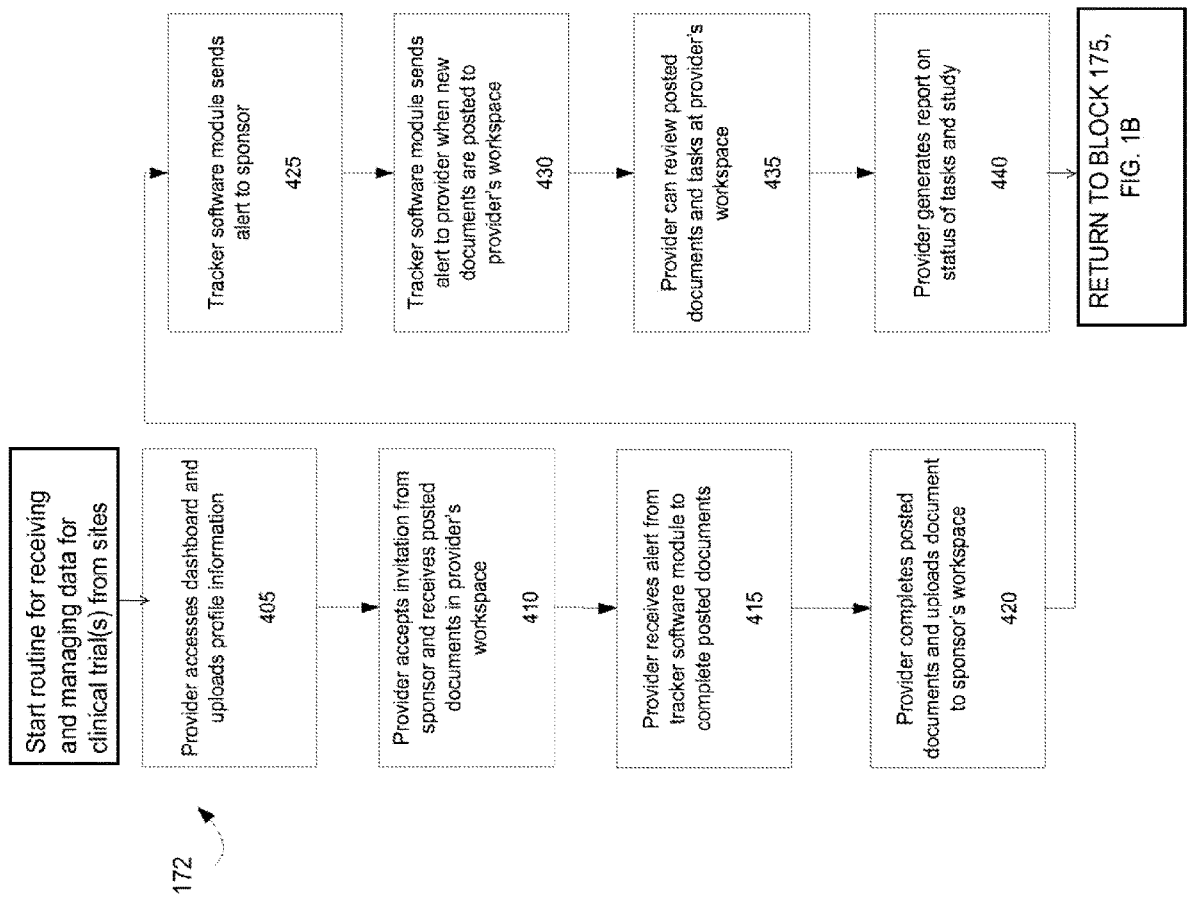
FIG. 4 illustrates a submethod or routine of FIG. 1B for receiving and managing data for clinical trials from sites via the computer network.

FIG. 4 illustrates a submethod or routine 172 of FIG. 1B for receiving and managing data for clinical trials from sites 165, 170 via the computer network 161. Beginning with block 405, an investigative site (investigative site computing device) 165, 170 may access the dashboard module 125 and upload profile information about the site 165, 170. This profile information can be stored in a repository such as data storage device 150A.

In block 410, the site 165, 170 may accept an invitation from the sponsor 180 to provide services for the clinical trial study. The site 165, 170 may also receive access to documents associated with the clinical study which are posted to the site's workspace, such as illustrated in FIG. 20 described below.

Typically, a site 165, 170 may also receive an alert concerning the documents newly posted to the site's workspace as illustrated in block 415 and illustrated in FIG. 20. The site (operator of site computing device) 165, 170 may complete the posted documents and any action items associated with those documents in block 420. The tracker module 120 can then upload the completed documents to sponsor's workspace, such as illustrated in FIG. 19 described below. In block 425, the tracker module 120 may send an alert to a sponsor (sponsor computing device) 180. In block 430, the tracker module 120 can send an alert to the site 165, 170 or other organization computing devices 185 when new documents associated with the next step of the clinical study are posted to the a site's or another provider's workspace maintained on the tracker server 110.

The responsible party may then review and complete the newly posted documents as well as any related tasks using the workspace maintained on the tracker server 110 and the dashboard module 125 in block 435. While not required, as illustrated in block 440, a provider, such as sites 165, 170 or another organization 185, may also use the dashboard module 125 to generate reports concerning the status of documents and tasks associated with the clinical study.

Referring now to FIG. 5, this figure illustrates exemplary data 500 that may be provided by a sponsor 175 for a proposed clinical trial. This data 500 generally corresponds with block 103 of method 102 described above in connection with FIG. 1B.

Such data 500 may include, but is not limited to, a title for a clinical trial, an abstract that summarizes areas to be covered by the proposed clinical trial as well as the solution (i.e. drug, method, medical procedure, medical device, etc.) to a problem that is identified. The data 500 may include characteristics of proposed, ideal patients or test subjects that are needed for the clinical trial. The data 500 may also comprise key terms 505 which are provided by the sponsor 175 of the clinical trial. The key terms 505 may generally correspond with block 550 of routine block 106 as illustrated in FIG. 1C.

In the exemplary embodiment illustrated in FIG. 5, the exemplary data 500 is for a proposed clinical trial entitled, "New surgical technique for low cervical section." The data 500 may comprise an abstract which provides a high level description of the new surgical technique. The data 500 includes information of desired proposed patients. For this exemplary clinical trial illustrated, the desired patient characteristics may include patient gender (i.e. women), patient age (i.e. 22-32 years), relevant medical condition or prognosis (i.e. pregnant), relevant medical restrictions (i.e. no psychiatric illness, never had a cesarean section for birth delivery, etc.). Other desired characteristics for patients are possible and are included within the scope of this disclosure.

In the exemplary embodiment illustrated in FIG. 5, the sponsor 175 of the clinical trial may, at the sponsor's option, provide one or more key terms 505. For the example in FIG. 5, the key term 505 provided is "Low cervical section." A key term 505 is generally a word or phrase that may be relevant to how a medical condition is coded by medical professionals when treating a medical condition. A sponsor may or may not provide one or more key terms 505 when data 500 about a proposed clinical trial is provided to the tracker server 110.

Figure 6A:
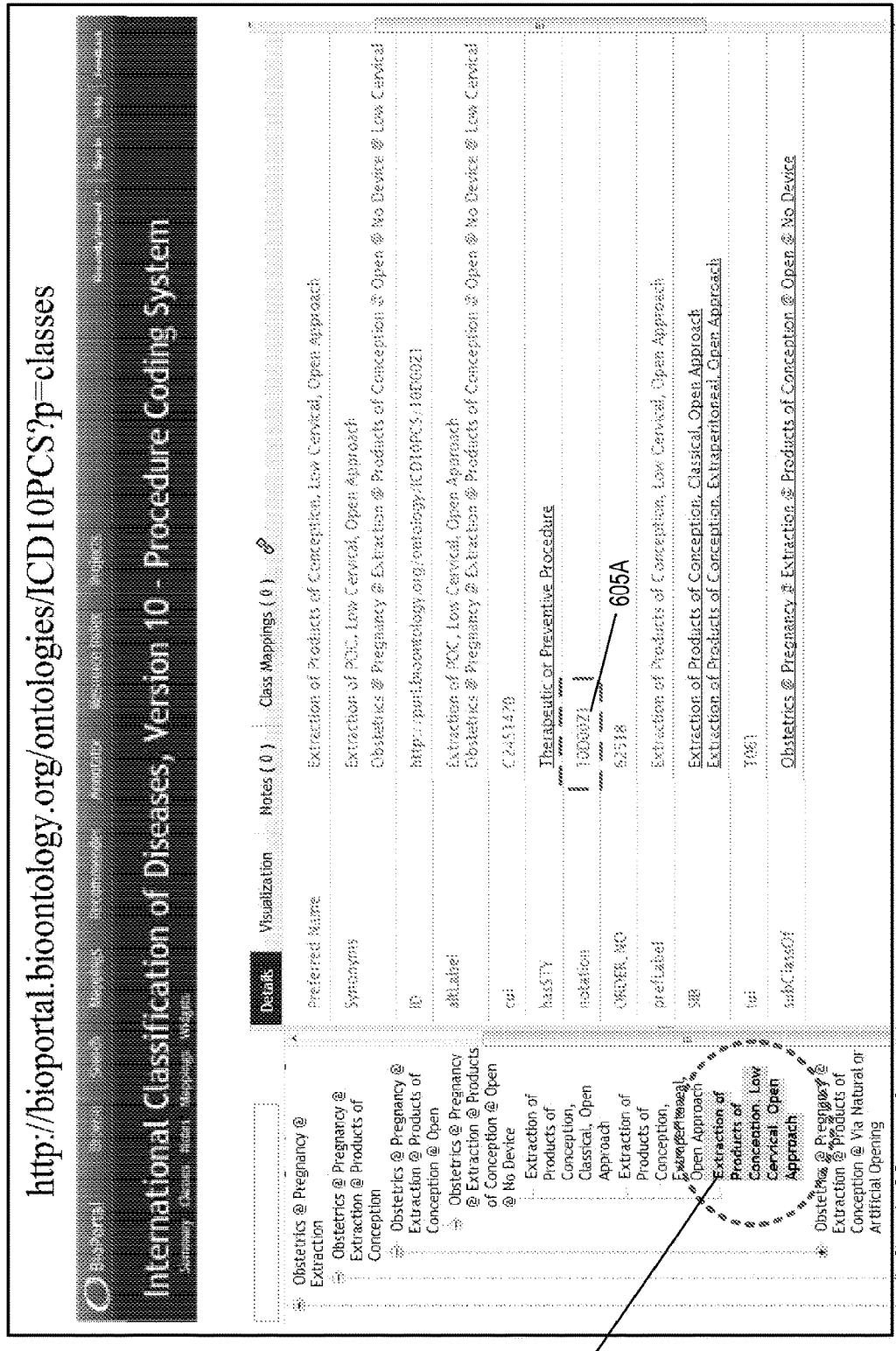
FIG. 6A illustrates an exemplary excerpt from a first biomedical database for determining one or more numeric or alphanumeric codes that will become part of a HOM bool.

Referring now to FIG. 6A, this figure illustrates an exemplary excerpt from a first exemplary biomedical database 600 for determining one or more numeric or alphanumeric codes 605 that will become part of a HOM boot 700. FIGS. 6A-6B generally correspond to routine block 106 of method 102, and more specifically to block 553 of routine block 106.

The exemplary biomedical database 600A illustrated in FIG. 6A comprises an excerpt from the International Classification of Diseases (also known by the abbreviation ICD) which is the United Nations-sponsored World Health Organization's "standard diagnostic tool for epidemiology, health management and clinical purposes." The ICD is generally designed as a health care classification system, providing a system of diagnostic codes for classifying diseases, including nuanced classifications of a wide variety of signs, symptoms, abnormal findings, complaints, social circumstances, and external causes of injury or disease.

The system in ICD is generally designed to map health conditions to corresponding generic categories together with specific variations, assigning for these a designated code, up to six characters long. Thus, major categories are designed to include a set of similar diseases.

Using the key terms 505 supplied by the sponsor 175, generated by the tracker server 110, and/or those derived from another operator using tracker server 110, the numeric or alphanumeric codes 605 associated with the key terms may be found. In the exemplary database 600A, an index 602 for the categories within the database 600A may be provided.

In the exemplary embodiment illustrated, the entry 602A in the index 602 relevant to the key term 505 "low cervical section" is "Extraction of products of conception. Low cervical. Open approach." The alphanumeric code 605A corresponding to the entry 602A is "10D00Z1" which is the notation code in the ICD database 600A. One of ordinary skill the art will appreciate that other codes within the ICD biomedical database 600 may be used without departing from the scope of this disclosure. Further, other types of biomedical databases 600 may be employed as will be described in further detail below in connection with FIG. 6B.

Figure 6B:
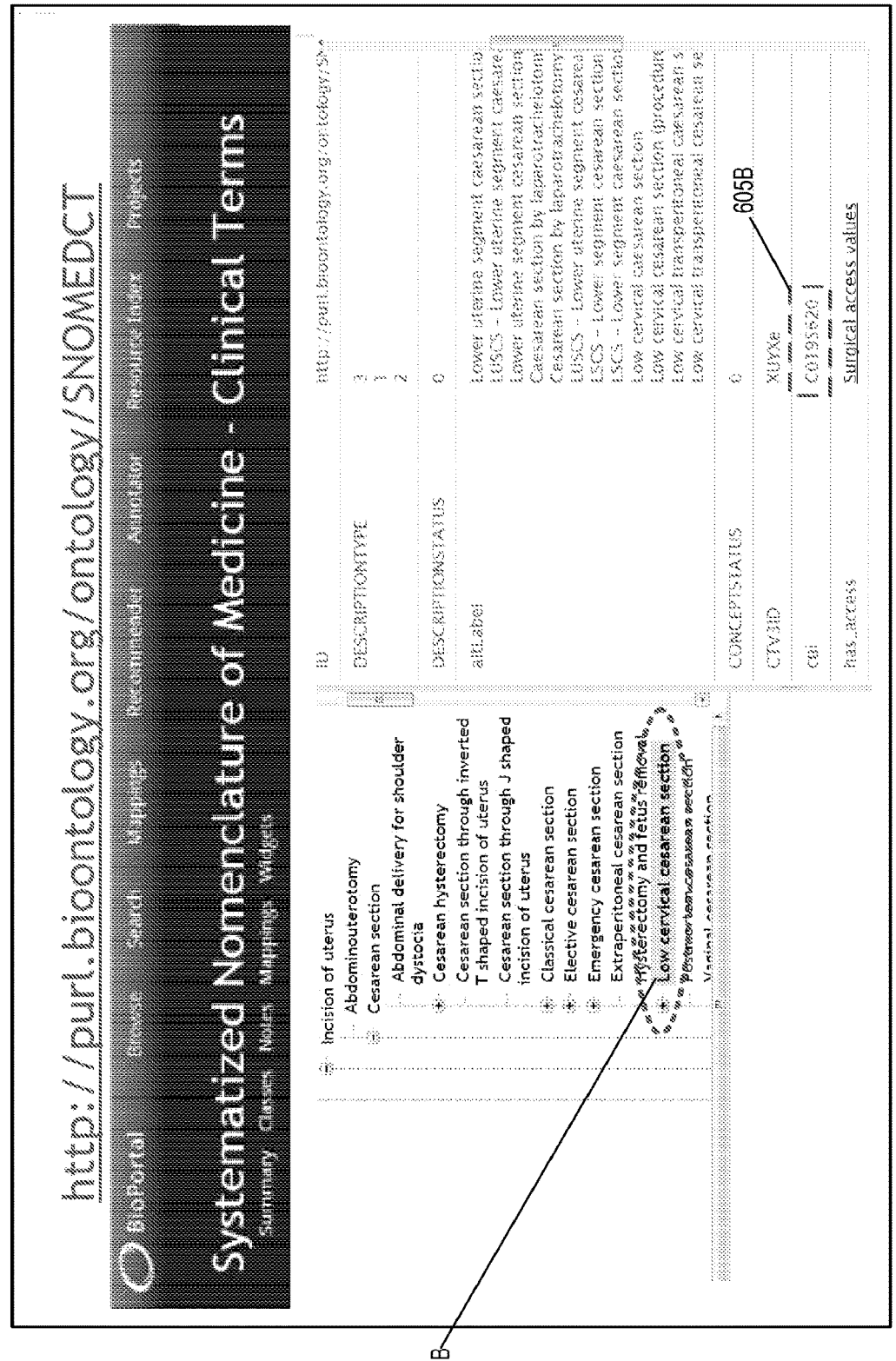
FIG. 6B illustrates an exemplary excerpt from a second biomedical database for determining one or more numeric or alphanumeric codes that will become part of a HOM bool.

Referring now to FIG. 6B, this figure illustrates an exemplary excerpt from an exemplary second biomedical database 600 for determining one or more numeric or alphanumeric codes 605 that will become part of a HOM boot 700 (See FIG. 7). As described above, FIG. 6B generally corresponds with routine block 106 of FIG. 1B, and more specifically, to block 553 of routine block 106 as illustrated in FIG. 1C.

The exemplary biomedical database 600B illustrated in FIG. 6B comprises an excerpt from the Systematized Nomenclature Of Medicine (SNOMED) Clinical Terms (CT) is a systematically organized computer processable collection of medical terms providing codes, terms, synonyms and definitions used in clinical documentation and reporting.

SNOMED CT is considered to be the most comprehensive, multilingual clinical healthcare terminology in the world. The primary purpose of SNOMED CT is to encode the meanings that are used in health information and to support the effective clinical recording of data with the aim of improving patient care. SNOMED CT provides the core general terminology for electronic health records. SNOMED CT comprehensive coverage includes: clinical findings, symptoms, diagnoses, procedures, body structures, organisms and other etiologies, substances, pharmaceuticals, devices and specimen.

Using the key terms 505 supplied by the sponsor 175, generated by the tracker server 110, and/or those derived from another operator using tracker server 110, the numeric or alphanumeric codes 605 associated with the key terms may be found. In the exemplary database 600B, an index 602 for the categories within the database 600B may be provided.

In the exemplary embodiment illustrated, the entry 602B in the index 602 relevant to the key term 505 "low cervical section" is "Low cervical caesarean section." The alphanumeric code 605B corresponding to the entry 602B is "C0195620" which is the concept unique identifier (CUI) in the SNOMED CT database 600B. One of ordinary skill in the art will appreciate that other codes within the SNOMED CT biomedical database 600B may be used without departing from the scope of this disclosure. Further, other types of biomedical databases 600 beyond the SNOMED CT database 600B and ICD database 600A may be employed as described above.

Referring now to FIG. 7, this figure illustrates an exemplary embodiment of HOM Boolean statements ("bools") 700 based on the data for the proposed clinical trial outlined in FIG. 5. as described above. FIG. 7 generally corresponds with routine block 106 of method 102 of FIG. 1B. And more specifically, FIG. 7 generally corresponds with block 556 of routine block 106 as illustrated in FIG. 1C.

As understood by one of ordinary skill in the art, HOM is a health ontology mapper system which facilitates the creation of an integrated data repository ("IDR") by directly addressing the need for terminology and ontology mapping in biomedical and translational sciences. HOM provides a discovery interface for a biomedical researcher to effectively understand and access the information residing within an IDR. HOM may facilitate distributed data queries by normalizing local representations of data into formal encoding standards. HOM translates terminologies into formal data encoding standards without altering the underlying source data.

Referring to line 720 of the HOM Boots 700 in FIG. 7, this line 720 defines the variable "U" for the HOM Bool lines 710 (HOM Bool2) and 715 (HOM Bool3). The variable "U" in line 720 has been defined by the SNOMED CT biomedical database 600B as described above.

Meanwhile, line 725 defines the variable "T" for HOM boot line 705 (HOM Bool1). Each line 705 through line 715 may comprise a combination of Boolean logic using the numeric or alphanumeric codes 605 uncovered from the respective biomedical databases 600A, 600B.

The HOM bools 700 may be transmitted from the tracker server 110 over the computer network 161 to respective sites 165, 170. Each site 165, 170 may have its own instance of a HOM client 111 which may be able to execute searches using the HOM bools 700. Alternatively, each site 165, 170 may access a HOM client 111 residing within the tracker server 110.

The HOM bools 700 allow each site 165, 170 to execute its own searches within its respective proprietary databases 150E, F which contain proprietary and confidential patient data. The HOM bools 700 search the proprietary databases 150E, F for patient data bearing the numeric or alphanumeric codes 605 derived from the biomedical databases 600.

Referring now to FIG. 8, this figure illustrates exemplary proprietary patient data 800 that may be maintained by sites 165, 170 as well as ACOs 175 in their respective proprietary databases 150B, C, D. These proprietary databases 150B, C, D are typically not available to the public and are restricted.

Patient data 800 illustrated in FIG. 8 generally corresponds to block 567 of subroutine 109 illustrated in FIG. 1D. Specifically, FIG. 8 illustrates patient data 800 for patients which has fields 805A, B that match the codes 605 which are the subject of the HOM bools 700 described above.

In the exemplary embodiment of FIG. 8, patient data 800A for a first patient 1 has a SNOMED CT field 805B that has a value of C019562 corresponding to the code 605B described above in connection with FIGS. 6-7. This means that patient 1 has a medical condition which was coded using the SNOMED CT biomedical database 600B illustrated in FIG. 6B.

Similarly, a second patient 2 having patient data 800B also had a medical condition coded using the ICD biomedical database 600 a illustrated in FIG. 6A. In the exemplary embodiment of FIG. 8, patient data 800B for a second patient 2 has an ICD field 805A that has a value of 10D00Z1 corresponding to the code 605A described above in connection with FIGS. 6-7. This means that the first patient 1 and the second patient 2 have data which matches the search codes 605 of the HOM bools 700 illustrated in FIG. 7. Patient 1 and patient 2 may be potential candidates for the proposed clinical trial based on this matched data.

The proprietary patient data 800 for each patient may include, but is not limited to, full legal name; postal mailing address which may include street address, city, state, zip code; Social Security number; insurance information such as a group number and a member number; government insurance information such as Medicare or Medicaid identification number; and detailed medical conditions.

As noted above, one of the key advantages of the inventive system 101 and method 102 is that each site 165, 170 and/or ACO 175 may search their own proprietary patient data 800 for matching medical records of patients. The matching medical records of patients may then be filtered by each site 165, 170 and/or ACO 175 so that sensitive and/or legally privileged information is not permitted to be transferred outside of the proprietary databases 150B, C, D. This filtering of matching medical record data of potential patients generally corresponds to block 572 of routine 109 as illustrated in FIG. 1D.

Figure 9:
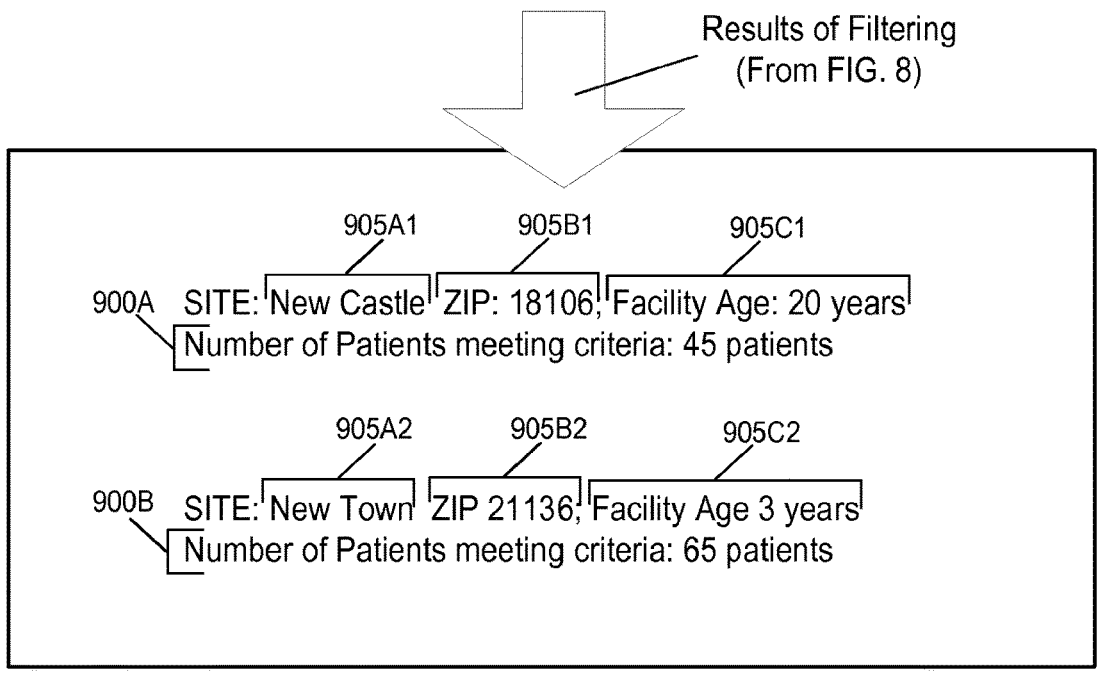
FIG. 9 illustrates filtered matching patient data that is generated during the method of FIG. 1B and also described during the routine of FIG. 1D.

Referring now to FIG. 9, this figure illustrates filtered matching patient data 900 that is generated during the method of FIG. 1B and also described during the routine of FIG. 1D. Specifically, the filtered matching patient data 900 corresponds with block 572 of routine 109 illustrated in FIG. 1D. The filtering in block 572 is performed by an ACO (ACO computing device) 175 or site (site computing device) 165, 170.

In the exemplary embodiment illustrated in FIG. 9, the filtered matching patient data 900 may comprise a raw number of patients matching at least one of the HOM bools 700 of FIG. 7. This means that most of the proprietary patient data 800 illustrated in FIG. 8 has been filtered or eliminated from the results of the HOM boot search conducted within the proprietary patient databases 150B, C, D during blocks 563 and 567 of routine 109 illustrated in FIG. 1D.

FIG. 9 further illustrates site data 905 that may be supplied by the sites 165, 170 and/or and ACO 175. The site data 905 may include, but is not limited to, an abbreviated facility name 905A, a postal zip code 905B, and approximate facility age/years in operation 905C. Other parameters are possible and are included within the scope of this disclosure. The site data 905 and the filtered matching patient data 900 are transmitted over the computer network 161 to the tracker server 110 which corresponds to routine block 109 of method 102 of FIG. 1B.

Referring generally to FIGS. 10-20, these figures convey various data that may be managed by the tracker server 110. Specifically, several of these figures convey data that may be displayed to sponsors 180, ACOs 175, and/or sites 165, 170 via user interfaces supported by the either the dashboard module 125 or the tracker module 120 or both, as will be apparent to one of ordinary skill in the art.

As noted above, FIG. 10 illustrates predetermined marketing data 1000 that may be prepared by a sponsor 180 in advance of conducting a patient search for a proposed clinical study. Predetermined marketing data 1000 may include, but is not limited to, monetary budget, number of patients needed, and other data relevant to the specifics of a particular clinical trial. For example, other data in the predetermined marketing data 1000 illustrated in FIG. 10 may include minimum number of patients from a particular geographic area (such as a postal zip code) and minimum number of patients who subscribe to a government program (such as Medicaid in the United States). Other data may be included within the predetermined market data 1000 and is within the scope of this disclosure. The market data 1000 may be keyed-in and stored and accessed by the tracker server 110.

Referring now to FIG. 11, this figure illustrates third party site data 1100 which may be added by the tracker server 110 to existing site data 905 and matching patient data 900. FIG. 11 generally corresponds with block 121 of method 102 described above.

The third party site data 1100 may be available from third-party databases 1100 such as illustrated in FIG. 1A. As noted previously, third party site data 1100 may include, but is not limited to, medical professional specialties, medical professional evaluations, faculty reviews, past or present litigation against sites and/or employees of a site, consumer/patient reviews, etc. The tracker server 110 may selectively add data fields from the third-party site data 1100 to the site data 905. The selective addition by the tracker server 110 may correspond with the HOM bools 700 so that only fields relevant to HOM bools 700 are supplied to a sponsor 180.

Referring now to FIG. 12, this figure illustrates a first ranked list 1200 of potential sites 165, 170 generated by the tracker server 110 for a proposed clinical trial based on the ranking of augmented matching patient data 900 and site data 905. FIG. 12 generally corresponds with block 124 of method 102 described above in connection with FIG. 1B.

In the exemplary embodiment illustrated in FIG. 12, the ranked list 1200 includes the Newtown facility having sixty-five patients ranked as number one; a New Castle facility having forty-five patients ranked as number two; and the San Diego facility having fifty-four patients ranked as number three.

Referring now to FIG. 13, this figure illustrates performance data 1300 which may be tracked by the tracker server 110. FIG. 13 generally corresponds with block 130 of method 102 illustrated in FIG. 1D. The performance data 1300 may be merged with the matching patient data 900 and site data 905 described above in connection with FIGS. 8-9. The performance data 1300 may comprise information that is routinely collected by the tracker server 110 while it manages the flow of information between clinical trial sites 165, 170 and sponsors 180 of those clinical trials via the computer network 161.

The performance data 1300 may include, but is not limited to, number of clinical trials that a particular site 165, 170 has used the tracker system 101, an overall percentage of timely data reporting for all trials which were monitored with the tracker system 101, and an overall satisfaction rating of a site 165, 170 from prior sponsors 180. Other performance data 1300 measured by the tracker server 110 is possible and is included within the scope of this disclosure. As described above in connection with block 130, the tracker server 110 may merge the performance data 1300 with the augmented matching patient data 900 and site data 905 described above.

Figure 14:
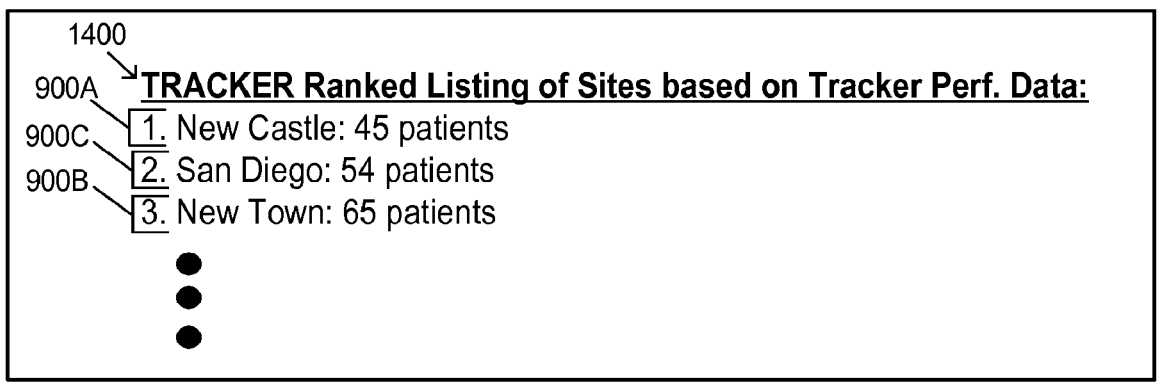
FIG. 14 illustrates a second ranked list of potential sites for a proposed clinical trial that is created based on a ranking of the merged augmented data illustrated in FIG. 13.

For now to FIG. 14, this figure illustrates a second ranked list 1400 of potential sites 165, 170 for a proposed clinical trial that is created based on a ranking of the merged augmented data 900, 905 and 1300 illustrated in FIG. 13. FIG. 14 generally corresponds with block 133 of method 102 illustrated in FIG. 1B.

This ranked list 1400 of potential sites 165, 170 for a proposed clinical trial may be generated by a tracker server 110 after evaluating the site performance data 1300 described above in connection with FIG. 13. Each sponsor 180 may assign different weightings for the performance data 1300 at their discretion.

In the exemplary embodiment illustrated in FIG. 14, the ranked list 1400 of sites 165, 170 based on the performance data 1300 includes the site of New Castle having forty-five patients ranked as number one, the San Diego clinic having fifty-four patients ranked as number two, and the Newtown site having sixty-five patients ranked as number three. As understood by one of ordinary skill the art, this ranking of sites 165, 170 may shift in response to any changes with respect to the weights assigned to the performance data 1300 illustrated in FIG. 13.

Figure 15:
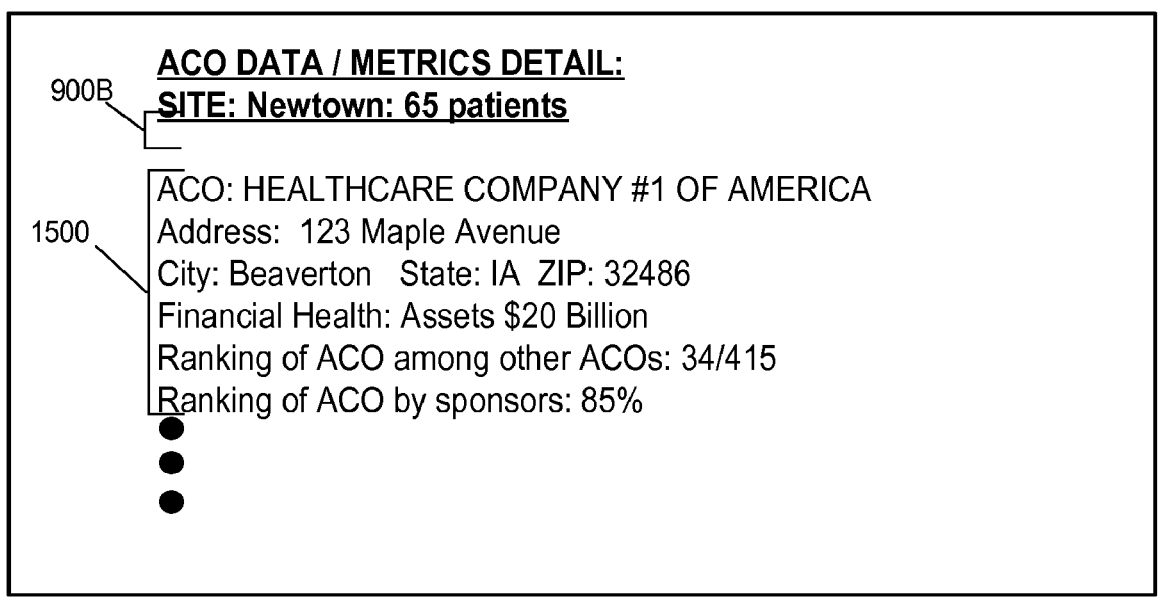
FIG. 15 illustrates ACO data that may be monitored and tracked with the tracker server of FIG. 1A.

Referring now to FIG. 15, this figure illustrates ACO data 1500 that may be monitored and tracked with the tracker server 110. FIG. 15 generally corresponds with block 142 of the method 102 as illustrated in FIG. 1B.

The ACO data 1500 may be retrieved by the tracker server 110 from a third-party database 1100 such as illustrated in FIG. 1B. Further, the tracker server 110 may also store its own ACO performance data similar to the performance data 1300 the tracker server 110 stores for respective sites 165, 170. The ACO data 1500 may include, but is not limited to, the full legal name of the ACO 175, any full legal names of holding companies with respect to the ACO 175, the financial health of the ACO 175, a ranking of the ACO 175 relative to other ACOs 175, and a ranking of an ACO 175 from sponsors 180, and other like data relevant to ACOs 175 as understood by one of ordinary skill the art.

Similar to the site performance data 1300 described above, the tracker server 110 may allow sponsors 180 to assign different weightings for each particular piece of ACO data 1500. In this way, each sponsor 180 may have different scaling/weightings for ACO data 1500 which are unique relative to other sponsors 180.

The scaling/weighting of ACO data 1500 by sponsors 180 is relevant to FIG. 16 described in further detail below. The tracker server 110 may rank the ACOs 175 associated with sites 165, 170 that had matching patient data 900 relative to the codes 605. The ranking may be based on the weightings assigned by a particular sponsor for the relevant ACO data 1500.

Figure 16:
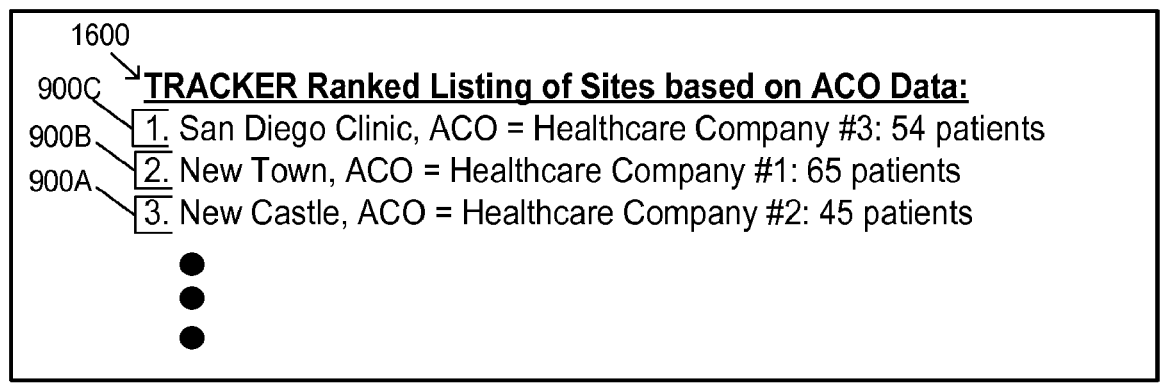
FIG. 16 illustrates a ranked listing of sites based on the ACO data illustrated in FIG. 15.

Referring now to FIG. 16, this figure illustrates a ranked listing 1600 of sites 165, 170 based on the ACO data 1500 illustrated in FIG. 15. FIG. 16 generally corresponds with block 145 of method 102 illustrated in FIG. 1B.

The ranked listing 1600 of sites 165, 170 may be generated by the tracker server 110 which scores sites 165, 170 based on weightings that may be assigned to the ACO data 1500 illustrated in FIG. 15. The ranked listing 1600 of sites 165, 170 based on the ACO data 1500 may be transmitted by the tracker server 110 over the computer network 161 to a sponsor 180.

In the exemplary embodiment illustrated in FIG. 16, the highest scoring site 165, 170 listed is the San Diego clinic having fifty-four patients which is owned/managed by an ACO of Health Care Company #3, while the second highest was New Town clinic having sixty-five patients which is owned/managed by an ACO of Healthcare Company #1, and the New Castle clinic having forty-five patients and an ACO of Healthcare Company #2 was ranked third.

Figure 17:
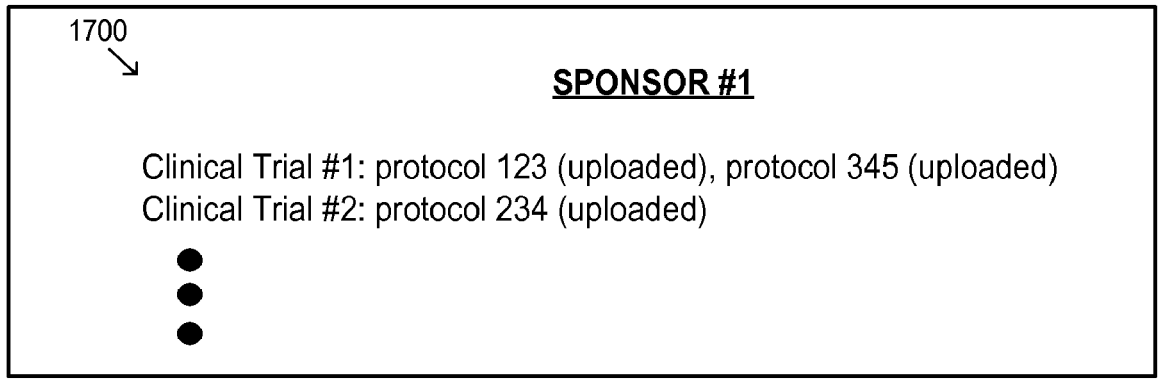
FIG. 17 illustrates one or more protocols which may be uploaded from a sponsor for distribution by the tracker server over the computer network to the sites.

Referring now to FIG. 17, this figure illustrates one or more protocols 1700 which may be uploaded from a sponsor 180 for distribution by the tracker server 110 over the computer network to the sites 165, 170. FIG. 17 generally corresponds to block 151 of method 102 illustrated in FIG. 1B.

A sponsor 180 may upload one or multiple protocols 1700 for one or multiple clinical trials. The protocols 1700 may comprise the procedures for executing a clinical trial by a clinical site 165, 170. Such procedures may govern how and when data is collected, stored, and shared using the tracker server 110.

Figure 18:
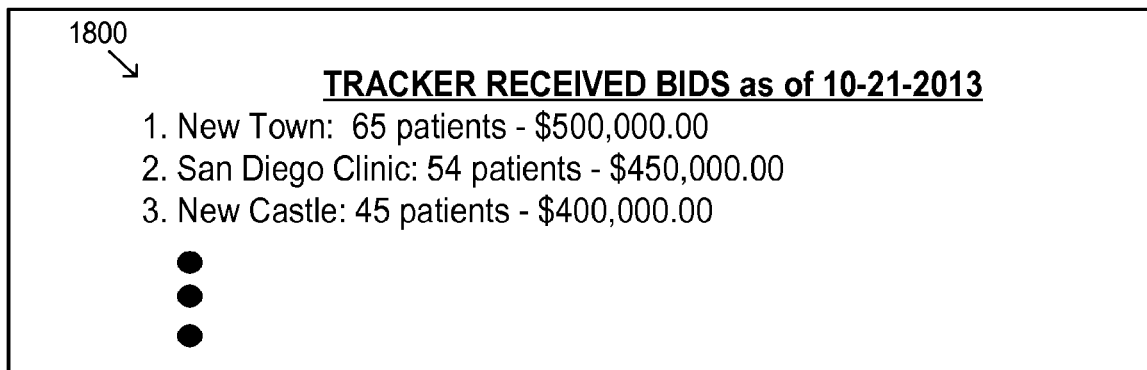
FIG. 18 illustrates bid/offer data uploaded by ACOs for a proposed clinical trial that are relayed to a sponsor via the computer network by the tracker server.

Referring now to FIG. 18, this figure illustrates bid/offer data 1800 uploaded by ACOs 175 for a proposed clinical trial that are relayed to a sponsor 180 via the computer network 161 by the tracker server 110. FIG. 18 generally corresponds to block 160 of method 102 illustrated in FIG. 1B.

The bid/offer data 1800 from ACO's 175 may be in the form of monetary bids, however, other data may be submitted/offered such as medical services and medical supplies which may be provided by a particular ACO 175 and/or site 165, 170. In the exemplary embodiment illustrated in FIG. 18, only monetary data in the form of U.S. dollars has been supplied. One of ordinary skill in the art recognizes that other currencies are included within the scope of this disclosures depending upon the nationality of the sponsors 180, ACOs 175, sites 165, 170, and the currency specified/preferred in the bid data supplied by the sponsors 180 to the clinic sites 165, 170 and ACOs 175.

In the exemplary embodiment, the New Town clinic has submitted the highest bid of $500,000.00 with the San Diego clinic following second with a bid of $450,000.00 and the New Castle clinic following third with a bid of $400,000.00. The bidding process may be open or closed as specified by a particular sponsor 180.

In an open bidding process, the bid/offer data 1800 may be public and an may be transmitted by the tracker server 110 over the computer network 161 to all of the sites 165, 170 and ACO's 175. In a close bid, the bid/offer data 1800 may be kept private by a sponsor 180 so that the bid/offer data 1800 received by the tracker server 110 is only relayed to the sponsor 180 of the proposed clinical trial via the computer network 161.

Referring now to FIG. 19, this figure illustrates a user interface 1900 that may be accessed over the computer network 161 by one or more sponsors 180. FIG. 19 generally corresponds with block 175 of method 102 illustrated in FIG. 1B.

The user interface 1900 manages clinical data received from clinical sites 165, 170 via the computer network 161. The user interface may comprise a status graph 1905 which highlights current status of a plurality of clinical sites 165, 170 which may be managed by a sponsor 180. In addition to sponsors 180 that may utilize the user interface 1900, contract research organizations (CROs) may also subscribe to the tracker server 110 and may manage clinical sites 165, 170 with the user interface 1900.

The status graph 1905 which highlights status information for a plurality of sites 165, 170 may comprise a pie chart as understood by one of ordinary skill the art. However, other types of charts besides pie charts for conveying information are well within the scope of this disclosure. In the exemplary embodiment illustrated in FIG. 19, the status graph 1905 indicates that there are nine sites 165, 170 in activation; there are two sites 165, 170 which have been released; there are three sites 165, 170 which have been dropped; and there are no (zero) sites 165, 170 which are in a hold status. It is recognized that other types of information besides the exemplary status information enumerated above may be tracked with the status graph 1905.

In addition to status information, the user interface 1900 may also convey progress data 1910 for multiple sites 165, 170 as well as individual sites 165, 170. In the exemplary embodiment illustrated in FIG. 19, the progress data 1910B comprises a timeline with certain events/milestones listed which are based on the protocol for a particular clinical study.

In addition to progress data 1910, the user interface 1900 may also convey details about each respective site 165, 170. For example, user interface 1900 may identify the names of principal investigators (PIs) 1915 for each site 165, 170; notes and communications 1920 from each site 165, 170; documents 1925 relevant to each site 165, 170; and submissions 1930 originate in from each site 165, 170. Other data such as actual measurements received for clinical data and the like may be conveyed and managed with the user interface 1900 as understood by one of ordinary skill the art.

Referring now to FIG. 20, this figure illustrates a user interface 2000 that may be accessed over the computer network 161 by a single or individual clinical site 165, 170. FIG. 20, like FIG. 19, generally corresponds with block 175 of method 102 illustrated in FIG. 1B.

The user interface 2000 manages clinical data received from a single clinical site 165, 170 via the computer network 161 (compared to multiple sites 165, 170 which are managed with user interface 1900 described above in connection with FIG. 19). The user interface 2000 may track data fields similar to those of FIG. 19, such as, but not limited to, nodes and communications 1920; documents 1925; submissions 1930; and staff 2005.

In the exemplary embodiment illustrated in FIG. 20, the documents category/tab 1925 has been selected so that a plurality of documents 2010 being managed by a single clinical site 165, 170 are displayed.

Similar to the user interface 1900, the user interface 2000 may also track progress data 1910 that may comprise a timeline. This progress data 1910 is specific to a single clinical site 165, 170 and it may also list a plurality of milestones/events and corresponding milestone dates. In the exemplary embodiment illustrated in FIG. 20, the principal investigator (PI) 1935 for a particular site 165, 170 may be listed in the top left portion of user interface 2000. In addition to the name of the principal investigator 1935, the user interface 2000 and may also displayed various other status information such as the country in which the clinical trial is being conducted as well as which sponsor or contract research organization is monitoring the progress of the clinical trial or study. See for example fields generally designated as 2015 in user interface 2000.

In a document send and receive aspect of embodiments of the invention, sponsor initiated document functionality of the web-based dashboard of FIGS. 19 and 20 includes, for example, associating documents with tasks and associating tasks with documents and deadlines such as illustrated by progress data 1910 of FIGS. 19-20 which is provided as a timeline according to one exemplary embodiment.

Adding documents to a task; sending a document from study document details; specifying the investigative site 165, 170 and principal investigator 1935 who will be responsible for a document; reviewing documents on an investigative site's document list; and returning documents.

In the document send and receive aspect, site-initiated document functionality of the dashboard module 125 includes, for example, adding new documents to a document list and sending documents from investigative site document lists; responding to document functionality of the dashboard includes, for example, responding from document details of an investigative site's document list and declining or forwarding documents; and signing document functionality of the dashboard includes, for example, electronic signing of documents.

The tracker software module 120 can be used to track a variety of tasks associated with a study as illustrated in FIGS. 19-20. For example, the tracker software module 120 can be used to track initial steps in the start-up of a study to ensure an investigative site 165, 170 is ready to be activated.

As another example, once an investigative site 165, 170 or some other provider 185 of services has been activated, the tracker software module 120 can be used to monitor ongoing tasks. The tracker software module 120 can provide a variety of useful functions for managing the various steps of a clinical trial study. For example, the tracker software module 120 can be associated with particular documents in a study workspace and can identify: i) who uploaded the document, ii) when it was uploaded, iii) any notes posted about the document, and iv) all information for each version of the document. The tracker software module 120 can have documents associated with its standard workflow as well as unique documents for particular clinical trials or other purposes.

The users who are permitted to associate documents with the tracker software module 120 can be controlled with various permission levels. In a typical embodiment, the tracker software module 120 is used to track documents that sponsors 180 have posted for an investigative site 165, 170 to complete. The sponsor 180 can receive an alert from the tracker software module 120 when an investigative site 165, 170 or other provider 185 has completed a document. If the sponsor 180 is not satisfied with the completed document, the tracker software module 120 can be used to reject the document and send an alert to the investigative site 165, 170 or other provider 185 to revise the document.

The tracker software module 120 also permits designation of a team lead for a sponsor 180 and a team lead for an investigative site 165, 170. Tasks managed by the tracker software module 120 can be assigned by default to the team leads for the sponsor 180 and the investigative site 165, 170 or can be customized and assigned to particular people associated with the sponsor 180 and the investigative site 165, 170.

Once a task has been assigned, it can also be reassigned to another person using the tracker software module 120. In addition to managing the status of tasks, the tracker software module 120 can control access to documents and information both from the sponsor workspace perspective and from the investigative site workspace perspective. Access can be controlled in a variety of ways including by setting permission levels, by controlling which users are invited to participate in a study, by granting access to certain parts of a study, and by assigning responsibility for tasks.

For example, a manager associated with the sponsor 180 or the investigative site 165, 170 can set and control the permission levels associated with each of the documents related to a clinical trial study. The user interface 1900 of FIG. 19 and user interface 2000 of FIG. 20 can list these permission levels which can be selected by a manager. The tracker software module 120 controls access to documents by applying the permission levels to the profile set up for each user accessing the sponsor workspace or the investigative site workspace.

As another example, the tracker software module 120 can be used to grant a new invitee to a study access to certain information relating to the initial steps, but not to more sensitive financial information associated with the study or to information relevant to later steps of the study. The tracker software module 120 also maintains an audit trail of which users were assigned permission to access particular documents.

In one exemplary embodiment, where a sponsor 180 is working with multiple investigative sites 165, 170, typically the members of the sponsor team would be given access to all of the documents for each of the investigative sites 165, 170. In contrast, each member of an investigative team typically would only be given access to the documents associated with their investigative team and would not be given access to documents associated with another investigative team.

In other embodiments, the sponsor 180 can restrict the access of its team members to selected documents, tasks, or steps within a study or across studies. Similarly, members of the investigative site team can be granted only limited access to a subset of information associated with a clinical study.

Each clinical study can be divided into steps and each step of the study can have certain associated tasks. When a task is ready to be started, the tracker software module 120 can send an alert in the form of a brief message to the person responsible for the task. Other team members of the user can also be set up to receive alerts.

Typically, via the dashboard module 125, which can generate user interface 1900 of FIG. 19, a sponsor 180 will have access to a number of filters that may be applied against a pre-defined or pre-specified population associated with one or more investigative sites 165, 170 (e.g., the service provider directory). In accordance with one range of embodiments, the population may comprise a group comprising providers or members relative to server 110. Application of one or more of the filters is effective to identify a desired subset of the total population associated with the site.

Such filters may act based upon pre-defined, selectable, or customizable criteria of interest to users of server 110. In accordance with a range of embodiments, the filters are specifically tailored to various aspects of the clinical trial start-up process, with sufficient granularity to promote ease of use. Filter sets involving one or more aspects of a clinical trial start-up process may be provided.

In accordance with another range of embodiments, the filters and filter sets are customizable by site users (e.g., sponsors 180, ACOs 175, sites 165, 170). Once established, such filters and filter sets may be maintained for subsequent access and use via the dashboard module 120. By way of example only, and without limitation, examples of filters and filter sets include, but are not limited to:

Region (Africa, Americas, Asia, Europe)
Clinical Trial Phase (I, II, III, IV)
Therapeutic Specialty (Cardiology, Dental, Dermatology, etc.)
Services (Analytical, Biostatistics, etc.)
Investigative Sites (Site Type, Site Equipment, Site Facilities, etc.)
Clinical Research Organizations (Phase, Therapeutic Specialty, etc.)
Preclinical Research (Drug Discovery Services, Toxicology Services, etc.)
Contract Manufacturing (Product, Capacity, Compliance, etc.)
Consultants & Services (Professional Services, etc.)
Industry Organizations
Equipment and Supplies
Drug Discovery
Conferences Filtered results may be sorted by alphabetical name, by region, by rating, or by another predetermined criteria. Sort criteria also may be defined by each user and saved, so that such criteria may be accessed in the future via the dashboard module 120. Such customization may be evidenced, for example, by customizable tabs, column headings, or the like being displayed along with the results of the search.

For a particular population subset, partners may be compared based upon predefined criteria associated with information that may be found in a partner profile. A target group of partners (i.e. ACOs 175, sites 165, 170) may be identified either automatically (based for example upon a pre-specified criteria), or manually (based for example upon a simple review of the comparison results).

Once a target group of prospective providers is identified, an inquiry may be created via a site workflow. Inquiries may be standard template forms available for use into which some basic information may be inserted. Such information might include name, address, date of inquiry, due date for response, descriptive text, etc. Also, the ability to attach one or more files to an inquiry (e.g., a confidentiality agreement, a form, a request for information (RFI)) may be provided.

Alternately, inquiries may be built using a site "wizard" which enables users (sites 165, 170; ACOs 1750 to select from a number of predefined elements (e.g., questions, text passages, etc.) to "build" an inquiry semi-automatically. In accordance with another range of embodiments, the wizard may guide the user through one or more subject matter areas including such elements, questions, passages, etc., and upon completion of the guided exchange between user and site, generate an inquiry. In accordance with a further range of embodiments, the wizard may permit a user to customize such questions, passages, etc. The inquiries generated from any of such steps may be saved for later review, editing, use, etc.

Sponsors 180 using a site 165, 170 as described herein typically may send via the server 110 one or more inquires to sites 165, 170 and ACOs 175. The inquiry may be standard form of inquiry that is sent to multiple providers (sites 165, 170 and/or ACOs 175) with the same content, format, etc., or the inquiry may be tailored in one or more respects based upon the characteristics of the provider recipient(s). Where a member (i.e. a sponsor 180, an ACO 175, and/or sites 165, 170) desires to contact a provider that is not a member, the server 110 may provide a workflow for inviting the non-member provider to become a member relative to the server 110.

Such an invitation may include at least a portion of the information from or associated with the sponsor inquiry. In some instances, the non-member provider will be unable to view the member communication without first becoming a member of the server 110, first claiming and editing the non-member provider's profile, etc. stored within server 110, which typically would occur in response to one or more invitations to the non-member provider resulting from such workflow.

Communications such as those referred to above between a provider and a member may be in the form of an email message. Where a provider is not a member with respect to the server 110, the email received by the non-member provider may include only a portion of the communication that the sponsor desires to send, and thus might be characterized as a "teaser" for encouraging greater participation with the server 110 by the non-member provider. Communications also may be in the form of a web-based posting of information coupled with an email notification of the post's existence and location. Other forms of communication of the availability of new information also are possible.

In accordance with one range of embodiments, the email communication to a member or provider may comprise notice of the availability on the server 110 of information from a sponsor 180. In such instances, a member or provider would need to navigate to the server 110 and login on the server 110 to retrieve available sponsor information. Such navigation may occur, for example, by the email notice including a direct link to a server login page.

In accordance with one range of embodiments, the tracker server 110 becomes the vehicle through which users communicate with one another. The tracker server 110 automatically tracks the status of the various information exchanges between users. Where multiple users have been contacted, the status of the communications within the group of users is tracked and reported, e.g., to display the number of users for which no response to an inquiry has been received. Where information is transferred involving the server 110, the server 110 may capture all or a portion of it for the population of one or more directories managed by the directory module 116.

The directories managed by the directory module 116 may be organized in a standard form (e.g., corresponding to a protocol for information transfer), custom form (e.g., to meet the needs of a particular user), or a combination of both. The tracker server 110 thus may provide one or more interfaces for the exchange of information between such directories and a separate program, site, organization or other such tool, solution, entity, etc. For example, and without limitation, upon receipt of instructions from a user, the server 110 may automatically port information to a clinical trial management system (i.e., a CTMS software solution) for use therein.

The steps and functions as described herein thus automate a process 102 which heretofore has been accomplished only through cumbersome, manually-performed actions. Tremendous savings in terms of time and cost may be realized with use of the systems 101 and methods 102 herein described. That is, this method 10 and system 10 promotes effective and efficient communication between those entities involved in the clinical trial start up process.

Figure 21:
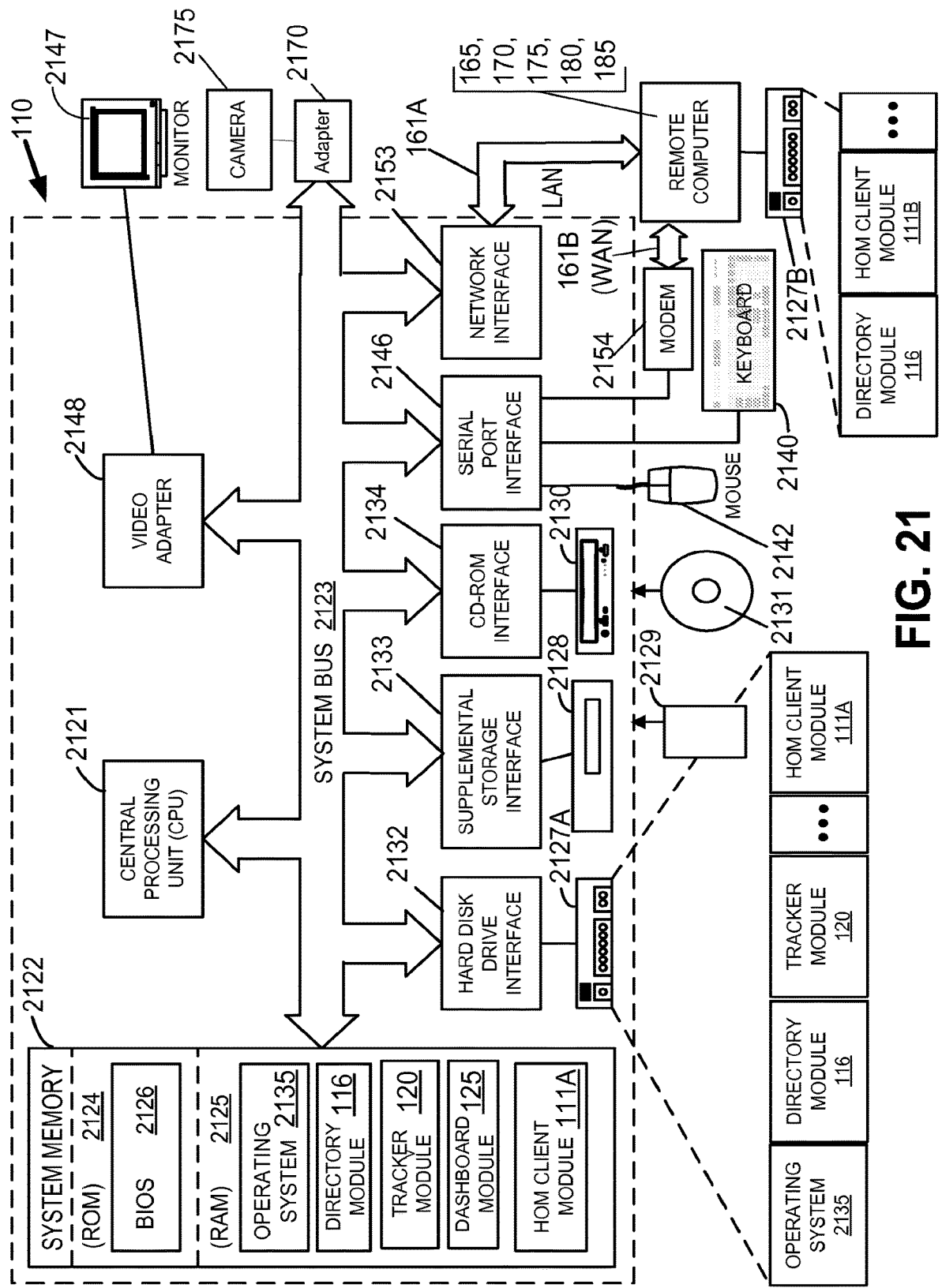
FIG. 21 illustrates a functional block diagram of a general purpose computing device, such as the server of FIG. 1A, that can be used in the system and method for identifying investigative sites in a clinical trial and centrally managing data received from the investigative sites.

Referring now to FIG. 21, this figure is a functional block diagram of a general purpose computing device, such as the server of FIG. 1A, and can be used in the system 101 and method 102 for identifying investigative sites in a clinical trial and centrally managing data received from the investigative sites. The exemplary operating environment for the system 101 of FIG. 1A described above includes a general-purpose computing device in the form of a conventional computer 110.

Generally, the computer 110 includes a processing unit 2121, a system memory 2122, and a system bus 2123 that couples various system components including the system memory 2122 to the processing unit 2121.

The system bus 2123 may be any of several types of bus structures including a memory bus or memory controller, a peripheral bus, and a local bus using any of a variety of bus architectures. The system memory includes a read-only memory (ROM) 2124 and a random access memory (RAM) 2125. A basic input/output system (BIOS) 2126, containing the basic routines that help to transfer information between elements within computer 110, such as during start-up, is stored in ROM 2124.

The computer 110 can include a hard disk drive 2127A for reading from and writing to a hard disk, not shown, a supplemental storage drive for reading from or writing to a removable supplemental storage 2129 (like flash memory and/or a USB drive) and an optical disk drive 2130 for reading from or writing to a removable optical disk 2131 such as a CD-ROM or other optical media. Hard disk drive 2127A, supplemental storage 2128, and optical disk drive 2130 are connected to system bus 2123 by a hard disk drive interface 2132, a supplemental storage drive interface 2133, and an optical disk drive interface 2134, respectively.

Although the exemplary environment described herein employs hard disk 2127A, removable magnetic disk 2129, and removable optical disk 2131, it should be appreciated by those skilled in the art that other types of computer readable media which can store data that is accessible by a computer, such as magnetic cassettes, flash memory cards, digital video disks, Bernoulli cartridges, RAMs, ROMs, and the like, may also be used in the exemplary operating environment without departing from the scope of the invention. Such uses of other forms of computer readable media besides the hardware illustrated will be used in internet connected devices such as in cellular phones and/or personal digital assistants (PDAs).

The drives and their associated computer readable media illustrated in FIG. 21 provide nonvolatile storage of computer-executable instructions, data structures, program modules, and other data for computer or client device 100A. A number of program modules may be stored on hard disk 2127, supplemental storage 2129, optical disk 2131, ROM 2124, or RAM 2125, including, but not limited to, an operating system 2135, directory module 116, tracker module 120, dashboard module 125, and the HOM client module 111A.

Program modules include routines, sub-routines, programs, objects, components, data structures, etc., which perform particular tasks or implement particular abstract data types. Aspects of the present invention may be implemented in the form of a downloadable, client-side, directory modules 116, tracker modules 120, dashboard modules 125, and HOM client modules 111 which are executed by the computer 110 in order to track data for clinical trials.

A user or operator may enter commands and information into computer 110 through input devices, such as a keyboard 2140 and a pointing device 2142. Pointing devices may include a mouse, a trackball, and an electronic pen that can be used in conjunction with an electronic tablet. Other input devices (not shown) may include a microphone, joystick, game pad, satellite dish, scanner, or the like. These and other input devices are often connected to processing unit 2121 through a serial port interface 2146 that is coupled to the system bus 2123, but may be connected by other interfaces, such as a parallel port, game port, a universal serial bus (USB), or the like.

The display 2147 may also be connected to system bus 2123 via an interface, such as a video adapter 2148. The display 2147 can comprise any type of display devices such as a liquid crystal display (LCD), a plasma display, an organic light-emitting diode (OLED) display, and a cathode ray tube (CRT) display.

A camera 2175 may also be connected to system bus 2123 via an interface, such as an adapter 2170. The camera 2175 can comprise a video camera such as a webcam. The camera 2175 can be a CCD (charge-coupled device) camera or a CMOS (complementary metal-oxide-semiconductor) camera. In addition to the monitor 2147 and camera 2175, the server 110, comprising a computer, may include other peripheral output devices (not shown), such as speakers and printers.

The computer 110 may operate in a networked environment using logical connections to one or more remote computers, such as the sites 165, 170, ACOs 175, sponsors 180, and other computing devices 185. A remote computer 165, 170, 175, 180, 185 may be another personal computer, a server, a mobile phone, a router, a network PC, a peer device, or other common network node. While these remote computing devices 165, 170, 175, 180, 185 typically include many or all of the elements described above relative to the server computer 110, only a memory storage device 2127B has been illustrated in the Figure.

The logical connections depicted in FIG. 21 include a local area network (LAN) 161A and a wide area network (WAN) 161B. Such networking environments are commonplace in offices, enterprise-wide computer networks, intranets, and the Internet as described above in connection with FIG. 1A.

When used in a LAN networking environment, the computer 110 is often connected to the local area network 161A through a network interface or adapter 2153. When used in a WAN networking environment, the computer 110 typically includes a modem 2154 or other means for establishing communications over WAN 161B, such as the Internet. Modem 2154, which may be internal or external, is connected to system bus 2123 via serial port interface 2146. In a networked environment, program modules depicted relative to the computer 110, or portions thereof, may be stored in the remote memory storage device 2127B. It will be appreciated that the network connections shown are exemplary and other means of establishing a communications link between the computers 110, 165, 170, 175, 180, 185 may be used.

Moreover, those skilled in the art will appreciate that the present invention may be implemented in other computer system configurations, including hand-held devices, multi-processor systems, microprocessor based or programmable consumer electronics, network personal computers, mini-computers, mainframe computers, and the like.

The invention may also be practiced in distributed computing environments, where tasks are performed by remote processing devices that are linked through a communications network. In a distributed computing environment, program modules may be located in both local and remote memory storage devices.

With respect to the software or programs described above in connection with the various process flows, such as the flow chart of FIG. 1B, certain steps in the processes or process flows described in this specification naturally precede others for the invention to function as described. However, the invention is not limited to the order of the steps described if such order or sequence does not alter the functionality of the invention.

That is, it is recognized that some steps described in the process flow diagrams may performed before, after, or parallel (substantially simultaneously with) other steps without departing from the scope and spirit of the invention. In some instances, certain steps may be omitted or not performed without departing from the invention. Further, words such as "thereafter", "then", "next", etc. are not intended to limit the order of the steps. These words are simply used to guide the reader through the description of the exemplary method.

Additionally, one of ordinary skill in programming is able to write computer code or identify appropriate hardware and/or circuits to implement the disclosed invention without difficulty based on the flow charts and associated description in this specification, for example.

Therefore, disclosure of a particular set of program code instructions or detailed hardware devices is not considered necessary for an adequate understanding of how to make and use the invention. The inventive functionality of the claimed computer implemented processes is explained in more detail in the above description and in conjunction with the Figures which may illustrate various process flows.

In one or more exemplary aspects, the functions described may be implemented in hardware, software, firmware, or any combination thereof.

If implemented in software, the functions may be stored on or transmitted as one or more instructions or code on a computer-readable medium. Computer-readable media include both computer storage media and communication media including any medium that facilitates transfer of a computer program from one place to another.

A storage media may be any available media that may be accessed by a computer. By way of example, and not limitation, such computer-readable media may comprise RAM, ROM, EEPROM, CD-ROM or other optical disk storage, magnetic disk storage or other magnetic storage devices, or any other medium that may be used to carry or store desired program code in the form of instructions or data structures and that may be accessed by a computer.

Also, any connection is properly termed a computer-readable medium. For example, if the software is transmitted from a website, server, or other remote source using a coaxial cable, fiber optic cable, twisted pair, digital subscriber line ("DSL"), or wireless technologies such as infrared, radio, and microwave, then the coaxial cable, fiber optic cable, twisted pair, DSL, or wireless technologies such as infrared, radio, and microwave are included in the definition of medium.

Disk and disc, as used herein, includes compact disc ("CD"), laser disc, optical disc, digital versatile disc ("DVD"), floppy disk and blu-ray disc where disks usually reproduce data magnetically, while discs reproduce data optically with lasers. Combinations of the above should also be included within the scope of computer-readable media.

Although selected aspects have been illustrated and described in detail, it will be understood that various substitutions and alterations may be made therein without departing from the spirit and scope of the present invention.

What is claimed is:

1. A computer-implemented method, performed by a computing system comprising a tracker server, for identifying one or more investigative sites of a clinical trial, the computer-implemented method comprising:
   receiving, by the tracker server, proposed clinical trial data from a communications network, the proposed clinical trial data comprising medical terms describing at least one of drugs, medical conditions, physical characteristics of ideal patients, and gender of ideal patients; the proposed clinical trial data being presented in a prose form of text describing an objective for the clinical trial;
   deriving, by the tracker server, at least one key biomedical word based on the proposed clinical trial data by matching a list of key biomedical words against the proposed clinical trial data, each key biomedical word comprising a word relevant to a type of medicine associated with the proposed clinical trial;
   conducting, by the tracker server, a search in a biomedical database using the at least one key biomedical word to uncover one or more alphanumeric codes used in clinical documentation of medical conditions;
   generating, by the tracker server, a health ontology mapper (HOM) boolean logic statement based on the one or more alphanumeric codes uncovered using the at least one key biomedical word, wherein the HOM boolean logic statement is generated to comprise computer code statements configured to be executed for searching patient data;
   transmitting, by the tracker server, the HOM boolean logic statement over the communications network to a remote client computer associated with an investigative site to cause the remote client computer to execute a search within data storage devices for patient data that matches the HOM boolean logic statement, wherein the patient data is proprietary relative to the investigative site;
   filtering the matching patient data by the remote client computer to remove restricted patient data, and the remote client computer transmitting the filtered matching patient data over the communications network;
   receiving, by the tracker server, the filtered matching patient data transmitted by the remote client computer over the communications network;
   generating, by the tracker server, a list of one or more proposed investigative sites based on the filtered matching patient data and displaying the list on a dashboard of a display on a computing device;
   receiving, via the dashboard on the computing device, a selection of one or more investigative sites;
   in response to the selection, transmitting protocol data and bid data by the tracker server over the communications network to the one or more selected investigative sites;
   in response to the tracker server receiving a bid on the proposed clinical trial over the communications network from a first selected investigative site, provide an option on the dashboard to accept the bid;
   wherein the tracker server centrally manages bids and data received from the one or more investigative sites; and
   in response to the tracker server receiving an acceptance of the bid from the dashboard, relaying acceptance of the bid over the communications network and activating the first selected investigative site corresponding to the accepted bid.

2. The method of claim 1, further comprising: receiving site data on the one or more proposed investigative sites based on the filtered matching patient data.

3. The method of claim 2, further comprising: comparing the filtered matching patient data and site data with predetermined marketing data.

4. The method of claim 3, determining with a processor if the proposed clinical trial is feasible based on the comparing of the filtered matching patient data with the predetermined marketing data.

5. The method of claim 4, further comprising: augmenting the data for the one more investigative sites with third-party data.

6. The method of claim 5, wherein the third-party data comprises at least one of medical professional specialties, medical professional evaluations, reviews of a facility, and a ranking of the investigative site and/or its medical professionals from patients.

7. The method of claim 5, further comprising: ranking the one or more proposed investigative sites based on the third-party data.

8. A computer system for identifying one or more investigative sites of a clinical trial and centrally managing data received from the one or more investigative sites, the computer system comprising:
   a central server having memory and a first processor, the first processor configured to receive and identify proposed clinical trial data from a communications network, the proposed clinical trial data comprising medical terms describing at least one of drugs, medical conditions, physical characteristics of ideal patients, and gender of ideal patients; the proposed clinical trial data being presented in a prose form of text describing an objective for the clinical trial;
   the first processor configured to derive at least one key biomedical word based on the proposed clinical trial data by matching a list of key biomedical words against the proposed clinical trial data, each key biomedical word comprising a word relevant to a type of medicine associated with the proposed clinical trial;
   the first processor configured to conduct a search in a biomedical database using the at least one key biomedical word to uncover one or more alphanumeric codes used in clinical documentation of medical conditions;
   the first processor configured to generate a health ontology mapper (HOM) boolean logic statement based on the one or more alphanumeric codes uncovered using the at least one key biomedical word, wherein the HOM boolean logic statement is generated to comprise computer code statements configured to be executed for searching patient data; and in response to the HOM Boolean logic statement being generated, the first processor further configured to transmit the HOM boolean logic statement over the communications network to a remote client computer to cause the remote client computer to execute a search within data storage devices for patient data that matches the HOM boolean logic statement;

the remote client computer of an investigative site comprising a memory and a second processor, the second processor configured to identify the matching patient data and filter the matching patient data to remove restricted patient data, the patient data being proprietary relative to the remote client computer; wherein the remote client computer is configured to transmit the filtered matching patient data over the communications network to the first processor of the central server;

the first processor further configured to, in response to receiving the filtered matching patient data from the communications network:

generating a list of one or more proposed investigative sites based on the filtered matching patient data and displaying the list on a dashboard of a display on a computing device;

receiving, via the dashboard on the computing device, a selection of one or more investigative sites;

in response to the selection, transmitting protocol data and bid data over the communications network to the one or more selected investigative sites;

in response to receiving a bid on the proposed clinical trial over the communications network from a first selected investigative site, provide an option on the dashboard to accept the bid;

wherein the central server centrally manages bids and data received from the one or more investigative sites; and in response to receiving an acceptance of the bid from the dashboard, relaying acceptance of the bid over the communications network and activating the first selected investigative site corresponding to the accepted bid.

9. The system of claim 8, wherein the first processor is configured to receive site data on the one or more proposed investigative sites based on the filtered matching patient data.

10. The system of claim 9, wherein the first processor is configured to compare the filtered matching patient data and site data with predetermined marketing data.

11. The system of claim 10, wherein the first processor is configured to determine if the proposed clinical trial is feasible based on the comparing of the filtered matching patient data with the predetermined marketing data.

12. The system of claim 11, wherein the first processor is configured to augment the data for the one more investigative sites with third-party data.

13. The system of claim 12, wherein the third-party data comprises at least one of medical professional specialties, medical professional evaluations, reviews of a facility, and a ranking of the investigative site and/or its medical professionals from patients.

14. The system of claim 12, wherein the first processor is configured to rank the one or more proposed investigative sites based on the third-party data.

* * * * *